US008916707B2

(12) United States Patent
Archer et al.

(10) Patent No.: US 8,916,707 B2
(45) Date of Patent: Dec. 23, 2014

(54) PROCESS

(71) Applicant: Johnson Matthey Public Limited Company, London (GB)

(72) Inventors: Nicolas Archer, Edinburgh (GB); Maureen Young, Edinburgh (GB); Timothy Davies, Edinburgh (GB); Amy Price, Edinburgh (GB); Michael Bease, Edinburgh (GB); Barbara Jamieson, Edinburgh (GB); Ewart Grant, Devens, MA (US); Brian Heinrich, Devens, MA (US); Saroop Matharu, Devens, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 13/957,943

(22) Filed: Aug. 2, 2013

(65) Prior Publication Data

US 2014/0045876 A1    Feb. 13, 2014

(30) Foreign Application Priority Data

Aug. 3, 2012  (GB) .................................. 1213874.9
Jun. 10, 2013  (GB) .................................. 1310275.1

(51) Int. Cl.
  *C07D 489/08*   (2006.01)
  *C07D 489/02*   (2006.01)

(52) U.S. Cl.
  CPC .................................. *C07D 489/08* (2013.01)
  USPC ............................................ 546/45; 546/44

(58) Field of Classification Search
  USPC .................................................... 546/45, 44
  See application file for complete search history.

(56) References Cited

U.S. PATENT DOCUMENTS

| | | | |
|---|---|---|---|
| 7,071,336 B2 | 7/2006 | Francis et al. | |
| 7,129,248 B2 | 10/2006 | Chapman et al. | |
| 7,153,966 B2 | 12/2006 | Casner et al. | |
| 7,674,799 B2 | 3/2010 | Chapman et al. | |
| 7,674,800 B2 | 3/2010 | Chapman et al. | |
| 7,683,072 B2 * | 3/2010 | Chapman et al. | ............. 514/282 |
| 7,875,623 B2 | 1/2011 | Shafer et al. | |
| 7,906,647 B2 | 3/2011 | Cox et al. | |
| 2005/0038251 A1 | 2/2005 | Francis et al. | |
| 2005/0222188 A1 | 10/2005 | Chapman et al. | |
| 2006/0111383 A1 | 5/2006 | Casner et al. | |
| 2006/0173029 A1 | 8/2006 | Chapman et al. | |
| 2007/0149559 A1 | 6/2007 | Shafer et al. | |
| 2008/0132703 A1 | 6/2008 | Cox et al. | |
| 2009/0156820 A1 | 6/2009 | Wang et al. | |
| 2010/0152449 A1 | 6/2010 | Chapman et al. | |

FOREIGN PATENT DOCUMENTS

| | | |
|---|---|---|
| CH | 75625 A | 9/1917 |
| CN | 101955484 A | 1/2011 |
| EP | 2377866 A1 | 10/2011 |
| IN | 1804DEL2008 A | 4/2010 |
| WO | 2006019364 A1 | 2/2006 |
| WO | 2007062184 A2 | 5/2007 |
| WO | 2008070656 A2 | 6/2008 |
| WO | 2008070658 A1 | 6/2008 |
| WO | 2009004491 A2 | 1/2009 |
| WO | 2011117172 A1 | 9/2011 |

OTHER PUBLICATIONS

International Search Report for corresponding Great Britain Patent Application No. GB1213874.9 dated Nov. 16, 2012.
Gongcheng, Huaxue Yu Shengwu, et al. "Synthesis of nalbuphine hydrochloride", (2007), 24 (9), 19-21, Zheng et al. and STN CASREACT Abstract accession No. 151:316337.
International Search Report and Written Opinion for corresponding PCT Patent Application No. PCT/US2013/053338 dated Sep. 16, 2013.
Krassnig, Roland et al., "Optimization of the Synthesis of Oxycodone and 5-Methyloxycodone", Archiv Der Pharmazie, vol. 329, No. 6, Jan. 1, 1996, pp. 325-326.

* cited by examiner

*Primary Examiner* — Charanjit Aulakh

(57) ABSTRACT

The present invention provides a process for preparing an oxycodone acid adduct, said process comprising hydrogenating an aqueous solution of 14-hydroxycodeinone and an acid to form a solution of the oxycodone acid adduct, wherein the hydrogenation is carried out at one or more temperatures greater than ambient temperature in the presence of a hydrogenation catalyst and hydrogen gas, wherein the solution of oxycodone acid adduct comprises 6α-oxycodol in an amount ≤about 0.800 area % as determined by HPLC.

26 Claims, 12 Drawing Sheets

PROCESS

FIELD OF THE INVENTION

The present invention concerns an improved process for the synthesis of oxycodone alkaloid and oxycodone salts, such as the hydrochloride, having improved impurity profiles.

BACKGROUND OF THE INVENTION

WO2005/097801 (to Euro-Celtique S.A.) describes processes for the preparation of oxycodone hydrochloride having less than 25 ppm of 14-hydroxycodeinone. The processes involve either:

(a) oxidising thebaine to form 14-hydroxycodeinone at a "suitable pH to minimize or eliminate" the production of 8,14-dihydroxy-7,8-dihydroxycodeinone in the 14-hydroxycodeinone. This process is not exemplified.

or (b) treating previously prepared and isolated oxycodone alkaloid or hydrochloride salt such that oxycodone hydrochloride having less than 25 ppm of 14-hydroxycodeinone is obtained. An exemplified method involves re-hydrogenating the previously prepared and isolated oxycodone alkaloid or hydrochloride salt.

WO2005/097801, however, does not describe a method for preparing oxycodone hydrochloride having less than 25 ppm of 14-hydroxycodeinone from conventionally prepared 14-hydroxycodeinone in a single step. Furthermore, WO2005/097801 is silent regarding the amounts of 6α-oxycodol produced according to the claimed processes.

SUMMARY OF THE INVENTION

We have developed an improved process which overcomes the disadvantages associated with prior art methods. The present process is suitable for the large-scale or industrial manufacture of oxycodone alkaloid and oxycodone salts.

DETAILED DESCRIPTION OF THE INVENTION

Figure 1:
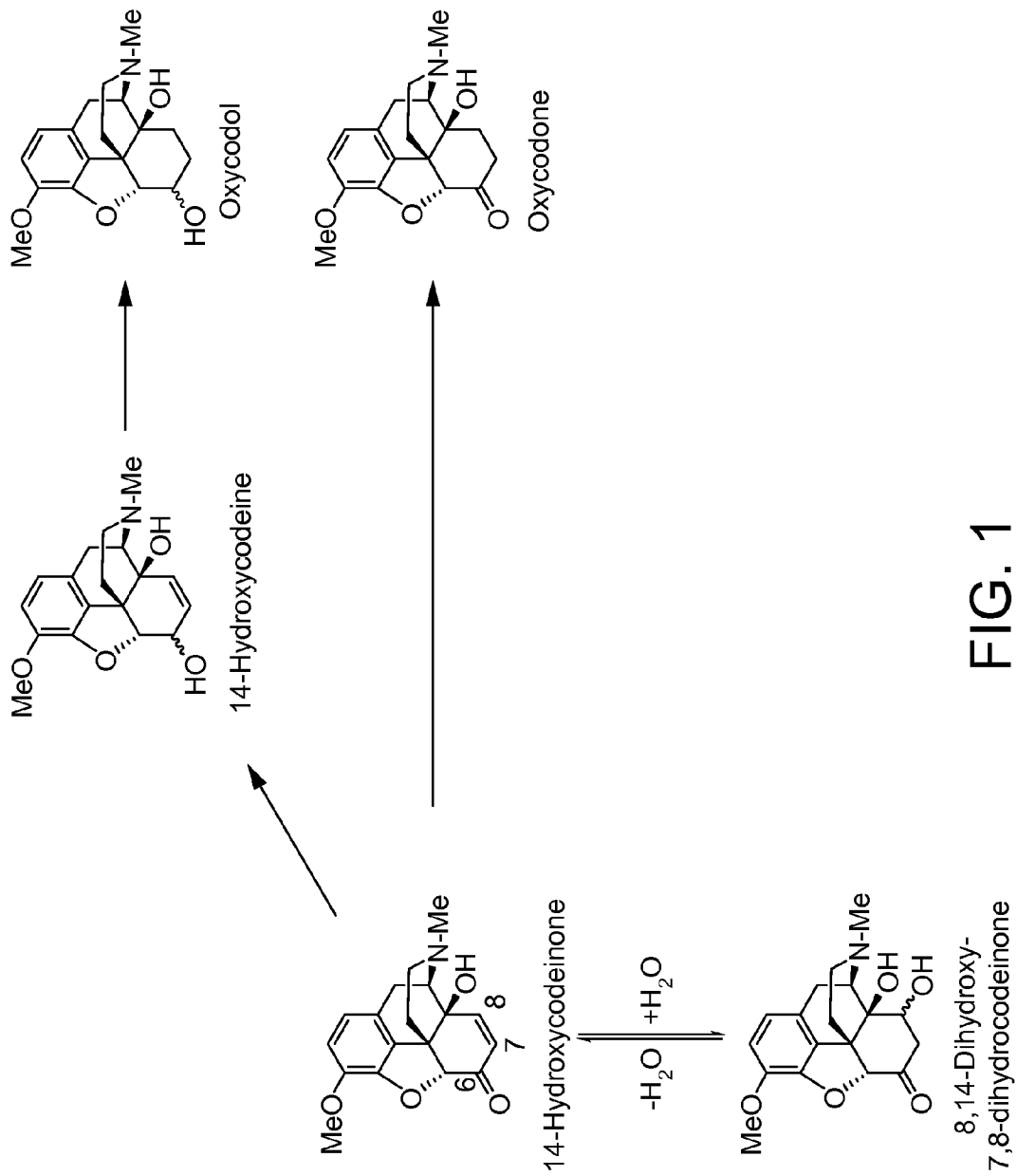
FIG. 1 illustrates the synthetic route of oxycodone.

In one aspect, therefore, the invention provides process for preparing an oxycodone acid adduct, said process comprising hydrogenating an aqueous solution of 14-hydroxycodeinone and an acid to form a solution of the oxycodone acid adduct, wherein the hydrogenation is carried out at one or more temperatures greater than ambient temperature in the presence of a hydrogenation catalyst and hydrogen gas, wherein the solution of the oxycodone acid adduct comprises 6α-oxycodol in an amount ≤about 0.800 area % as determined by HPLC.

The process comprises hydrogenating an aqueous solution of 14-hydroxycodeinone and an acid. The pH of the initial reaction mixture may be any suitable pH which does not adversely affect the impurity profile of the reaction. In one embodiment, the pH of the initial reaction mixture may be in the range of about ≥1.0 to about <7.0. In some embodiments, the pH may be ≥about 1.5. In some embodiments, the pH may be ≥about 2.0. In some embodiments, the pH may be ≤about 6.5. In some embodiments, the pH may be ≤about 6.0. In some embodiments, the pH may be ≤about 5.5. In one embodiment, the pH of the initial reaction mixture may be in the range of about ≥2.0 to about ≤about 5.5, such as about 5.0. The pH of the reaction mixture may increase during the course of the reaction and, if desired, the pH may be lowered through the addition of further acid or a solution of acid/water.

The acid may be selected from the group consisting of acetic acid, phosphoric acid, citric acid, tartaric acid, oxalic acid, hydrochloric acid and hydrobromic acid. In one embodiment, the acid is acetic acid. In another embodiment, the acid is phosphoric acid. In yet another embodiment, the acid is hydrochloric acid.

The solution of the oxycodone acid adduct formed corresponds with the acid utilised in the reaction. Thus oxycodone acetate corresponds with acetic acid, oxycodone phosphate with phosphoric acid, oxycodone citrate with citric acid, oxycodone tartrate with tartaric acid, oxycodone oxalate with oxalic acid, oxycodone hydrochloride with hydrochloric acid and oxycodone hydrobromide with hydrobromic acid.

Any suitable v/v ratio of water:acid may be used. For example, the v/v ratio of water:acid may be from about 10:0.01 to about 0.01:10, such as about 5.0:1 to about 5.5:1.

The ratio of acid:14-hydroxycodeinone may be in the range of about 1:2.0 g/g to about 1:2.5 g/g, such as about 1:2.15 g/g. The ratio of 14-hydroxycodeinone:water may be in the range of about 1:0.005 to about 1:10, such as about 1:0.01 to about 1:3.13 g/g. The quantities of water and/or acid are not particularly limiting provided there is enough water and/or acid to substantially dissolve the 14-hydroxycodeinone. In this regard, the inventors have found that minimal water may be added to reaction mixture and the hydrogenation of 14-hydroxycodeinone has been successfully performed to produce oxycodone acid adduct having a low level of 6α-oxycodol when the quantity of water added corresponded only to amount which would have been present in the water-wet catalyst. The quantity of water present in the catalyst and/or 14-hydroxycodeinone (which may also be used wet) may be taken into account when calculating the total quantity of water to be used.

The 14-hydroxycodeinone is substantially dissolved in the water and acid. The dissolution of the 14-hydroxycodeinone may be encouraged through the use of an aid such as stirring and/or sonication.

Conventionally, the hydrogenation of 14-hydroxycodeinone is carried out at an ambient temperature. By "ambient temperature", we mean a temperature of 30° C. or less. In the present process, however, the hydrogenation is carried out at one or more temperatures greater than ambient temperature i.e. greater than 30° C. and below the boiling point of the reaction mixture. The boiling point of the reaction mixture may vary depending on the pressure under which the hydrogenation reaction is conducted. In one embodiment, the hydrogenation may be carried out at one or more temperatures in the range of ≥about 75° C. to about ≤about 100° C. In some embodiments, the hydrogenation is carried out at one or more temperatures ≥about 76° C. In some embodiments, the hydrogenation is carried out at one or more temperatures ≥about 77° C. In some embodiments, the hydrogenation is carried out at one or more temperatures ≤about 95° C. In some embodiments, the hydrogenation is carried out at one or more temperatures ≤about 90° C. In some embodiments, the hydrogenation is carried out at one or more temperatures ≤about 85° C. In one preferred embodiment, the hydrogenation is carried out at one or more temperatures in the range of ≥about 77° C. to about ≤85° C., such as about 80° C.

In another embodiment, the hydrogenation may be carried out at one or more temperatures in the range of ≥about 55° C. to about ≤about 100° C. In some embodiments, the hydrogenation is carried out at one or more temperatures ≥about 56° C. In some embodiments, the hydrogenation is carried out at one or more temperatures ≥about 57° C. In some embodiments, the hydrogenation is carried out at one or more temperatures ≥about 58° C. In some embodiments, the hydrogenation is carried out at one or more temperatures ≥about 59° C. In some embodiments, the hydrogenation is carried out at one or more temperatures ≥about 60° C. In some embodiments, the hydrogenation is carried out at one or more temperatures ≤about 95° C. In some embodiments, the hydrogenation is carried out at one or more temperatures ≤about 90° C. In some embodiments, the hydrogenation is carried out at one or more temperatures ≤about 85° C. In one preferred embodiment, the hydrogenation is carried out at one or more temperatures in the range of ≥about 55° C. to about ≤85° C., such as about ≥about 60° C. to about ≤80° C.

The hydrogenation catalyst may be a heterogeneous or homogeneous catalyst, preferably a heterogeneous catalyst. The catalyst (whether heterogeneous or homogeneous) should be selected such that the catalyst preferentially reduces the double bond between C-7 and C-8 rather than reducing the C=O bond at C-6 (see FIG. 1). In one embodiment, the heterogeneous catalyst is a heterogeneous platinum group metal (PGM) catalyst, for example, a heterogeneous palladium or platinum catalyst. In one embodiment, the heterogeneous catalyst is a heterogeneous palladium catalyst. Examples of palladium catalysts include but are not limited to colloidal palladium, palladium sponge, palladium plate or palladium wire. Examples of platinum catalysts include but are not limited to colloidal platinum, platinum sponge, platinum plate or platinum wire.

The heterogeneous PGM metal catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$A_2O_3$, beta-$Al_2O_3$, gamma-$A_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon. An example of another heterogeneous PGM catalyst is platinum on carbon.

The catalyst loading may be up to about 20 mole %. In one embodiment, the catalyst loading may be up to 10 mole % and, in another embodiment, may be in the range of about 0.1-10.0 mole %.

While it is typically sufficient for a single charge of hydrogenation catalyst to be added to the reaction mixture, a second or further charge may be added and the hydrogenation continued if it has been determined (e.g. via in-process analysis) that the reaction has not gone to completion and starting material remains.

There is no particular limitation on the pressure at which the hydrogenation is carried out. In this regard, the hydrogenation may conveniently be carried out with an initial hydrogen pressure in the range of up to about 100 psi e.g. about 40±5 psi.

In carrying out the process of the invention at a temperature greater than ambient temperature, it is possible to obtain an oxycodone acid adduct with an improved impurity profile. In one embodiment, it is possible to significantly reduce the levels of 6α-oxycodol, an impurity which must be controlled to particular levels specified in Official Monographs such as the US Pharmacopeia. For example, the USP 33 Reissue for Oxycodone Hydrochloride specifies that the acceptance criterion for 6α-oxycodol cannot be more than 0.25%. It is important to recognise, however, that the Official Monograph relates to oxycodone hydrochloride which is suitable for formulation and subsequent administration to a person. In this respect, the oxycodone hydrochloride ultimately prepared in a production campaign may have undergone several (or, indeed, many) processing treatments in order to reduce the level of 6α-oxycodol, as well as other impurities, to sufficiently acceptable low levels in order to conform to the required standard. The processing treatments therefore can typically result in extended processing times on plant and loss in product yield. In carrying out the process of the present invention, however, the formation of 6α-oxycodol can be minimised in the reaction which produces it as an impurity, thus reducing the requirement for further processing. The levels of 6β-oxycodol do not appear to be significantly affected by the hydrogenation conditions of the present invention. In this respect, the levels of 6β-oxycodol generally remain low from experiment to experiment.

Without wishing to be bound by theory, 6-oxycodol does not appear to be generated from oxycodone (see FIG. 1). Instead, it appears to be produced from 14-hydroxycodeinone which is reduced to 14-hydroxycodeine and it is this latter compound which results in the formation of 6-oxycodol. The hydrogenation process of the present invention therefore appears to influence the 14-hydroxycodeinone→14-hydroxycodeine→6-oxycodol pathway such that the quantity of 6α-oxycodol formed is at a reduced level. Accordingly, the hydrogenation process of the present invention may immediately meet the acceptance criterion specified for 6α-oxycodol in a single step thus improving the overall synthetic route of the oxycodone acid adduct (e.g. oxycodone hydrochloride) by increasing the yield of the desired product of the hydrogenation reaction (by decreasing the quantity of 14-hydroxycodeinone lost to impurity formation), as well as reducing or eliminating the requirement for later processing treatments.

The present invention provides a process wherein the solution of oxycodone acid adduct comprises 6α-oxycodol in an amount ≤about 0.800 area % as determined by HPLC. In some embodiments, the solution of oxycodone acid adduct comprises 6α-oxycodol in an amount ≤about 0.700 area % as determined by HPLC. In some embodiments, the solution of oxycodone acid adduct comprises 6α-oxycodol in an amount ≤about 0.600 area % as determined by HPLC. In some embodiments, the solution of oxycodone acid adduct comprises 6α-oxycodol in an amount ≤about 0.500 area % as determined by HPLC. In some embodiments, the solution of oxycodone acid adduct comprises 6α-oxycodol in an amount ≤about 0.400 area % as determined by HPLC. In some embodiments, the solution of oxycodone acid adduct comprises 6α-oxycodol in an amount ≤about 0.300 area % as determined by HPLC. In some embodiments, the solution of oxycodone acid adduct comprises 6α-oxycodol in an amount ≤about 0.250 area % as determined by HPLC. In some embodiments, the solution of oxycodone acid adduct comprises 6α-oxycodol in an amount ≤about 0.225 area % as determined by HPLC. In some embodiments, the solution of oxycodone acid adduct comprises 6α-oxycodol in an amount ≤about 0.200 area % as determined by HPLC. In some embodiments, the solution of oxycodone acid adduct comprises 6α-oxycodol in an amount ≤about 0.175 area % as determined by HPLC. In some embodiments, the solution of oxycodone acid adduct comprises 6α-oxycodol in an amount ≤about 0.150 area % as determined by HPLC. In some embodiments, the solution of oxycodone acid adduct comprises 6α-oxycodol in an amount ≤about 0.100 area % as determined by HPLC. A suitable HPLC method for determining the amount of 6α-oxycodol is, for example, the Oxycodone Hydrochloride PhEur 6.0 Method detailed below. An alternative suitable HPLC method is HPLC Method 2 also described below.

It has been found that in order to minimise the production of 6α-oxycodol, the reaction mixture is generally heated to temperature before the hydrogenation reaction starts. In this regard, the inventors have found that when the hydrogenation reaction commences at room temperature and the reaction mixture is heated after the uptake of hydrogen ceases, the amount of 6α-oxycodol is relatively high in the isolated oxycodone alkaloid. Example 7 describes such a reaction and it can be seen that the amount of 6α-oxycodol on reaction completion was 4.61% and was 2.40% in the isolated oxycodone alkaloid. In contrast, Example 2.1 describes a reaction according to the invention where the 6α-oxycodol is produced in the post-hydrogenation liquor in 0.170% and in the isolated base 0.088%.

Heating the reaction mixture to temperature may be carried out by purging the reaction vessel with one or more nitrogen/vacuum cycles (e.g. one, two, three or four cycles), optionally followed by one or more hydrogen/vacuum cycles (e.g. one, two or three cycles). On a small scale, the inventors do not believe the exposure of the reaction mixture to hydrogen in the purge cycles is detrimental to producing lower levels of 6α-oxycodol. On a larger, or indeed industrial scale, the hydrogen/vacuum cycles are generally not performed. During purging the reaction mixture may be agitated to encourage removal of dissolved oxygen. After the final purge cycle the vessel may be left under vacuum and agitated (by either stirring or shaking) whilst the vessel is heated. Once the reaction mixture reaches the desired temperature, the hydrogenation reaction may begin by exposing the reaction mixture to hydrogen gas.

Alternatively, the reaction mixture may be heated to the desired temperature and held at that temperature before exposing the reaction mixture to the hydrogen gas. In one embodiment, therefore, the reaction mixture may be held at one or more temperatures above ambient for up to about 1 minute or more before the hydrogen gas is added. In another embodiment, the reaction mixture may be held at one or more temperatures above ambient for up to about 15 minutes or more before the hydrogen gas is added. In yet another embodiment, the reaction mixture may be held at one or more temperatures above ambient for up to about 6 hours or more before the hydrogen gas is added.

The hydrogenation reaction is carried out for a period of time until it is determined that the reaction is complete. Completion of the reaction may be determined by in-process analysis or by identifying that there is no longer an uptake of hydrogen gas. Typically the hydrogenation is complete within about 1 or 2 hours, and in some embodiments, within about 30 minutes. The reaction mixture, however, may be held at temperature and pressure for up to about 24 hours.

On completion of the reaction, the reaction vessel may be cooled to ambient temperature and purged to remove excess hydrogen gas (or vice versa). The hydrogenation catalyst may be removed by any appropriate method, such as filtration, and the filtrate (containing the oxycodone acid adduct) may be further treated as desired.

In another embodiment, the process further comprises treating the solution of oxycodone acid adduct to form solid oxycodone acid adduct. Examples of solid oxycodone adducts include but are not limited to oxycodone acetate or oxycodone hydrochloride. If the hydrogenation is carried out in hydrochloric acid, solid oxycodone hydrochloride may be isolated from the reaction mixture. It is also envisaged that the solution of oxycodone acid adduct may undergo a salt exchange to form a solution of oxycodone acid adduct comprising a different acid. For example, a solution of oxycodone acetate may undergo a salt exchange to form a solution of oxycodone hydrochloride.

In yet another embodiment, the process further comprises treating the solution of oxycodone acid adduct with a base to form oxycodone alkaloid. An example of a suitable base is ammonium hydroxide. Sufficient base is typically added so that the oxycodone alkaloid precipitates out of solution. Generally, oxycodone alkaloid precipitate starts to become visible at about pH 7 and typically sufficient base is added to increase the pH to about 9. This ensures that the oxycodone alkaloid is in free base form, as well as allowing maximum recovery of the oxycodone alkaloid.

In another embodiment, the process further comprises treating the solid oxycodone acid adduct to form oxycodone alkaloid. This may be carried out by redissolving the solid oxycodone acid adduct to form a solution of oxycodone acid adduct and treating the solution with a base as described above. The oxycodone alkaloid may be collected (e.g. by filtration), optionally washed one or more times and dried.

In some embodiments, the oxycodone alkaloid comprises 6α-oxycodol in an amount ≤about 0.250 area % as determined by HPLC. In some embodiments, the oxycodone alkaloid comprises 6α-oxycodol in an amount ≤about 0.225 area % as determined by HPLC. In some embodiments, the oxycodone alkaloid comprises 6α-oxycodol in an amount ≤about 0.200 area % as determined by HPLC. In some embodiments, the oxycodone alkaloid comprises 6α-oxycodol in an amount ≤about 0.175 area % as determined by HPLC. In some embodiments, the oxycodone alkaloid comprises 6α-oxycodol in an amount ≤about 0.150 area % as determined by HPLC. In some embodiments, the oxycodone alkaloid comprises 6α-oxycodol in an amount ≤about 0.100 area % as determined by HPLC. A suitable HPLC method for determining the amount of 6α-oxycodol is, for example, either the Oxycodone Hydrochloride PhEur 6.0 Method or HPLC Method 2 detailed in the Examples below.

In yet another embodiment, the oxycodone alkaloid may be slurried with a liquid alcohol and heated with optional stirring. On cooling (with further stirring if desired), the oxycodone alkaloid may be collected (e.g. by filtration), optionally washed one or more times with an alcohol and dried. The alcohol may be a straight-chain, branched or cyclic $C_{1-10}$-alkanol and may be selected from the group consisting of methanol, ethanol, propanols (n- or i-), butanols (n-, i- or t-), pentanols, hexanols and heptanols. In one embodiment, the alcohol may be selected from the group consisting of ethanol and methanol. In one embodiment, the alcohol is ethanol. In another embodiment, the alcohol is Alcohol M, which is 96% ethanol denatured with 4% methanol. The inventors have found that treatment with the alcohol removes further 6α-oxycodol (if present).

Optionally or in addition, the oxycodone alkaloid may be crystallised or recrystallized from a suitable solvent mixture, such as dichloromethane/ethanol.

Other impurities which are also specified in the Official Monographs include α,β-unsaturated ketones (ABUKs), such as 14-hydroxycodeinone and codeinone. There has been much recent concern over ABUKs due to their proposed biological activities as genotoxins. As such, there is a continuing need to develop processes which produce low ABUK oxycodone alkaloid and low ABUK oxycodone salts, such as low ABUK oxycodone hydrochloride. Without wishing to be bound by theory, it appears that the 14-hydroxycodeinone which may be present as an impurity in oxycodone alkaloid or acid adduct thereof originates from two sources—firstly, residual unreacted 14-hydroxycodeinone starting material and secondly, indirectly from 8,14-dihydroxy-7,8-dihydrocodeinone which, it has been argued, converts to 14-hydroxycodeinone under acidic conditions (see FIG. 1). Thus, even if the reactions conditions are capable of driving a reaction to form oxycodone having <10 ppm of 14-hydroxycodeinone, the ABUK, 14-hydroxycodeinone, may be generated during salt formation via the dehydration of 8,14-dihydroxy-7,8-dihydrocodeinone. In this regard, 8,14-dihydroxy-7,8-dihydrocodeinone may be present in the hydrogenation of 14-hydroxycodeinone to oxycodone as it may be present as an impurity in the 14-hydroxycodeinone starting material. It may, therefore, be carried forward in the transformation of 14-hydroxycodeinone to oxycodone, as well as subsequent salt formation to form an oxycodone salt. Likewise, the ABUK codeinone may be generated during salt formation via the dehydration of the precursor 8-hydroxy-7,8-dihydrocodeinone (not shown in FIG. 1).

In one embodiment, therefore, the oxycodone acid adduct or oxycodone alkaloid prepared according to the present invention comprises ≤about 50 ppm of an α,β-unsaturated ketone, such as ≤about 25 ppm of an α,β-unsaturated ketone, for example, ≤about 15 ppm of an α,β-unsaturated ketone. In one preferred embodiment, the oxycodone acid adduct or alkaloid comprises ≤about 10 ppm of an α,β-unsaturated ketone. In another embodiment, the oxycodone acid adduct or alkaloid is substantially free of an α,β-unsaturated ketone. The α,β-unsaturated ketone may be selected from the group consisting of 14-hydroxycodeinone, codeinone and a mixture thereof. Without wishing to be bound by theory, it is believed that the temperature at which the present invention is carried out (i.e. greater than ambient temperature) is capable of simultaneously dehydrating 8,14-dihydroxy-7,8-dihydrocodeinone (to produce 14-hydroxycodeinone), hydrogenating 14-hydroxycodeinone (to form oxycodone), dehydrating 8-hydroxy-7,8-dihydrocodeinone, if present (to form codeinone) and hydrogenating codeinone, if present (to form hydrocodone).

In another aspect, the invention provides process for preparing an oxycodone acid adduct, said process comprising hydrogenating an aqueous solution of 14-hydroxycodeinone and an acid to form a solution of the oxycodone acid adduct, wherein the hydrogenation is carried out at one or more temperatures greater than ambient temperature in the presence of a hydrogenation catalyst and hydrogen gas, wherein the solution of the oxycodone acid adduct comprises less 6α-oxycodol than that produced on carrying out the hydrogenation at ambient temperature.

All of the embodiments described above, such as, the hydrogenation conditions, the hydrogenation catalyst or the minimisation in the level of 6α-oxycodol produced, generally likewise apply to this aspect of the invention.

In another aspect, the present invention provides a process for preparing an oxycodone acid adduct, said process comprising hydrogenating 14-hydroxycodeinone and an acid in a solvent comprising an alcohol and optionally water to form the oxycodone acid adduct, wherein the hydrogenation is carried out at one or more temperatures greater than ambient temperature in the presence of a hydrogenation catalyst and hydrogen gas, wherein the oxycodone acid adduct comprises less 6α-oxycodol than that produced on carrying out the hydrogenation at ambient temperature.

All of the embodiments described above, such as, the hydrogenation conditions, the hydrogenation catalyst or the minimisation in the level of 6α-oxycodol produced, generally likewise apply to this aspect of the invention.

The solvent comprises an alcohol and optionally water. The alcohol may be a straight-chain, branched or cyclic $C_{1-10}$-alkanol and may be selected from the group consisting of methanol, ethanol, propanols (n- or i-), butanols (n-, i- or t-), pentanols, hexanols and heptanols. In one embodiment, the alcohol may be ethanol.

As mentioned above, the hydrogenation is carried out at one or more temperatures greater than ambient temperature i.e. greater than 30° C. and below the boiling point of the reaction mixture. The skilled person would understand and take into account the pressure of the reaction and the effect that it may have on the boiling point of the reaction mixture.

In yet another aspect, the present invention provides an aqueous solution of oxycodone acid adduct comprising 6α-oxycodol in an amount ≤about 0.800 area % as determined by HPLC. In one embodiment, the oxycodone acid adduct is oxycodone acetate or oxycodone hydrochloride. In another embodiment, the aqueous solution of oxycodone acid adduct further comprises ≤about 25 ppm of an α,β-unsaturated ketone, preferably ≤about 10 ppm.

In another aspect, the present invention provides solid oxycodone acid adduct comprising 6α-oxycodol in an amount ≤about 0.800 area % as determined by HPLC, preferably ≤about 0.250 area %. In one embodiment, the oxycodone acid adduct is oxycodone acetate or oxycodone hydrochloride. In another embodiment, the solid oxycodone acid adduct further comprises ≤about 25 ppm of an α,β-unsaturated ketone, preferably ≤about 10 ppm.

In yet another aspect, the present invention provides solid oxycodone alkaloid comprising 6α-oxycodol in an amount ≤about 0.800 area % as determined by HPLC, preferably ≤about 0.250 area %. In one embodiment, the oxycodone alkaloid further comprises ≤about 25 ppm of an α,β-unsaturated ketone, preferably ≤about 10 ppm.

The invention will now be described by way of the following non-limiting Examples.

EXAMPLES

General

Analytical Methods
1. Oxycodone Hydrochloride PhEur 6.0 HPLC Method
Column: Symmetry C18 5 microns 15.0 cm×4.6 mm
Mobile phase: Prepare a solution as follows: dissolve 1.1 g sodium heptanesulphonate monohydrate in 1000 mL water, adjust to pH 2.0 with a 50% v/v solution of phosphoric acid.
: A 70 mL acetonitrile, 100 mL MeOH and 830 mL of the above solution.
: B 150 mL acetonitrile, 250 mL MeOH and 600 mL of the above solution.
Flow rate: 1.5 mL/minute
Temperature: 40° C.
Detector: UV @ 230 nm
Injection volume: 10 microliters
Run time: 65 minutes
Linear Gradient:

| Time (min) | A % v/v | B % v/v |
|---|---|---|
| 0 | 100 | 0 |
| 60 | 50 | 50 |
| 62 | 100 | 0 |
| 70 | 100 | 0 |

A blank 0.1 M HCl, 0.25 mg/mL standards of 14-hydroxycodeinone and codeinone, 0.58 μg/mL and 0.58 μg/mL of an oxycodol in 0.1M HCL standard were prepared and then analysed using the above method. ~1 mg/mL samples of the post hydrogenation liquors and isolated oxycodone alkaloid were also prepared in 0.1M HCl.

2. HPLC Method 2
2.1 Reagents and Materials:
(Equivalent reagents and materials may be substituted)

| | |
|---|---|
| Acetic Acid (HOAc) | J. T. Baker, HPLC Grade, |
| Acetonitrile (ACN) | Fisher Scientific, HPLC Grade |
| 1-Decanesulfanate, Sodium salt | Fluka, HPLC Grade |
| HPLC Mobile Phase Filters | EM Science 0.2μ PTFE |
| Hydrochloric Acid (HCl) | J T Baker, A.C.S. Reagent |
| 14-Hydroxycodeinone | Qualified Reference Standard |
| Methanol (MeOH) | Fisher Scientific, HPLC Grade |
| Oxycodone Hydrochloride | Qualified Reference Standard |
| Sodium Hydroxide (NaOH) | J. T. Baker, A.C.S. Reagent |
| Thebaine Bitartrate | Qualified Reference Standard |
| Triethylamine (TEA) | Fisher Scientific, HPLC Grade |
| Water ($H_2O$) | MilliQ, Model A10 Ultra Pure Water System |

2.2 Instrumentation:
(Equivalent instrumentation can be used)

| | |
|---|---|
| Detector | Waters, 2487 UV/VIS Detector |
| Chromatograph | Waters 2690 Separations Module |
| Data System | Millennium 32 C/S, current JM version |

2.3 Operating Conditions:
(Equivalent instrumentation can be used)

| | | | |
|---|---|---|---|
| Column | Phenomenex, Luna, $C_{18}$ (2), 3 μm, 100 × 4.6 mm | | |
| Injection Volume | 10 μL | | |
| Temperature | 35° C. | | |
| Detection | UV at 280 nm | | |
| Flow Rate | 1.5 mL/min | | |
| Linear Gradient | Time (min) | % MP A | % MP B |
| (Mixing) Conditions: | initial | 100 | 0 |
| | 20 | 90 | 10 |
| | 40 | 0 | 100 |
| | 45 | 0 | 100 |
| | 46 | 100 | 0 |
| | 55 | 100 | 0 |

2.4 Mobile Phase Preparation:
Mobile Phase (MP) A: Weigh 2.22 g of Decane Sulfonic Acid, Sodium Salt and transfer into a suitable 1 L flask. Transfer 750 mL purified water 100 mL MeOH and 150 mL ACN into the flask. Mix well to completely dissolve the ion-pairing salt. Add 20.0 mL of HOAc and 1.0 mL of TEA. Adjust the apparent pH to 3.5 with HOAc (or NaOH~1 N). Filter and degas the solution.
Mobile Phase (MP) B: Weigh 2.22 g of Decane Sulfonic Acid, Sodium Salt and transfer into a suitable 1 L flask. Transfer 450 mL $H_2O$, 400 mL MeOH, and 150 mL ACN into the flask. Mix well to completely dissolve the ion-pairing salt. Add 20.0 mL of HOAc and 1.0 mL of TEA. Adjust the apparent pH to 3.5 with HOAc (or NaOH~1 N). Filter and degas the solution.
Note: This will produce about 1 L of each mobile phase. If more/less is required, adjust the weights and volumes accordingly for each.

2.5 Diluent Preparation:
Using concentrated HCl and purified HPLC grade water, prepare a 0.1 N hydrochloric acid solution.

2.6 Approximate Retention Times of Known Analytes:

| Analyte | Approximate Retention Time (min) | RRT |
|---|---|---|
| 6α-Oxycodol | 11.4 | 0.58 |
| Oxycodone | 19.5 | 1.00 |
| 14-Hydroxycodeinone | 22.0 | 1.12 |
| Thebaine | 33.0 | 1.69 |

2.7 Sample Solution Preparation:
Filter approximately 10 mL of the reaction mixture, to remove catalyst, using a 0.45 m syringeless filter. Transfer approximately 0.10 mL (about 100 mg) of the filtrate into an HPLC vial. Transfer 1.0 mL of methanol into the vial and mix. Dilute to 2.0 mL with diluent and mix well.

2.8 Retention Time Markers:
Weigh approximately 10 mg of 14-Hydroxycodeinone and 6α-Oxycodol, 20 mg Oxycodone reference standard into a 50 mL volumetric flask. Add 5.0 mL of methanol and sonicate until all solids are dissolved. Do not sonicate for more than one minute. Dilute to volume with diluent and mix well.

2.9 System Equilibration:
After purging mobile phase through both reservoirs pump Mobile Phase B for at least 20 minutes. Switch to Initial assay conditions and pump for at least 20 minutes.

2.10 Procedure:
Separately inject: the diluent as a blank, the retention time marker and the sample solution.

2.11 System Suitability:
Make the necessary chromatographic adjustment(s) to achieve the necessary system suitability requirement.

2.11.1 Resolution:
The resolution between 14-Hydroxycodeinone and Oxycodone, in the retention time marker solution, should be NLT 2.0.
2.11.2 USP Tailing:
The USP tailing factor of the Oxycodone peak, in the retention time marker, should be between 0.5 and 2.0.
2.12 Calculations:
Subtract any artifact peak(s) found in the blank injection.
2.12.1 %14-Hydroxycodeinone Remaining: Normalized Peak Area %

$$\text{Area \% (14-Hydroxycodeinone)} = \frac{\text{Peak Area}_{14\text{-}hydroxycodeinone} \times 100}{(\text{Area}_{Oxycodone} + \text{Area}_{14\text{-}hydroxycodeinone})}.$$

2.12.2 % 6α-Oxycodol: Peak Area %

$$\text{Area \% (6}\alpha\text{-Oxycodol)} = \frac{\text{Peak Area}_{6\alpha\text{-}Oxycodol} \times 100}{\text{Total Area in chromatogram}}$$

2.12.3 Resolution:

$$\text{Resolution} = \frac{2(RT_{14\text{-}hydroxycodeinone} - RT_{Oxycodone})}{(W_{14\text{-}hydroxycodeinone} + W_{Oxycodone})}$$

Where:
RT=Retention Time in minutes.
W=Width of Peak (at 5% above the height) in minutes.
2.12.4 USP Tailing:
(at 5% above the baseline height)

$T = W_{0.05}/2f$

Where:
T=USP Tailing factor
$W_{0.05}$=width of the peak at 5% of its' height
f=distance from the peak maximum to the leading edge of the peak, the distance being measured at a point 5% of the peak height from the baseline.

Figure 2:
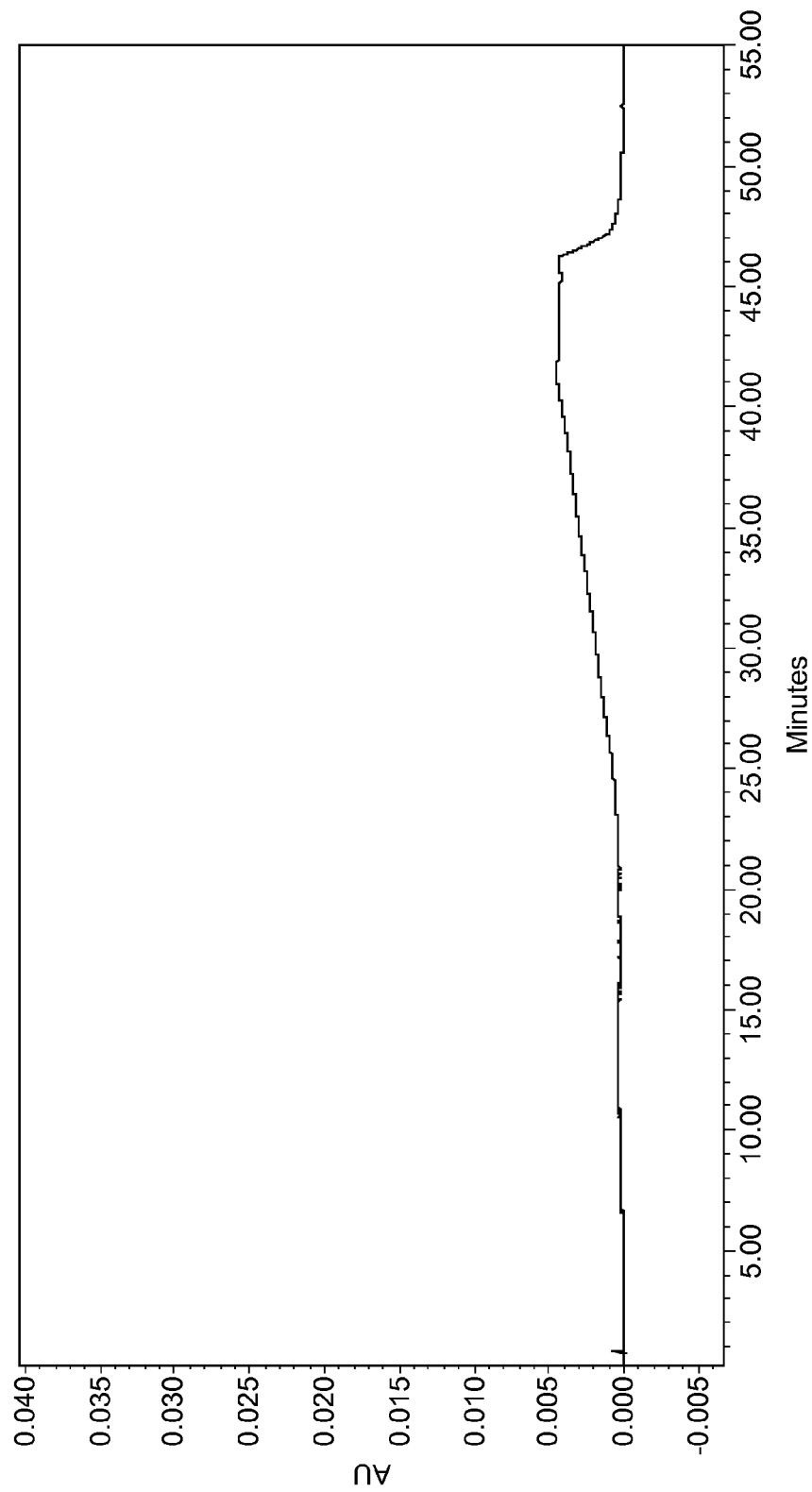
FIG. 2 illustrates a typical chromatogram using 0.1N HCl/water acid solution as blank.
Figure 3:
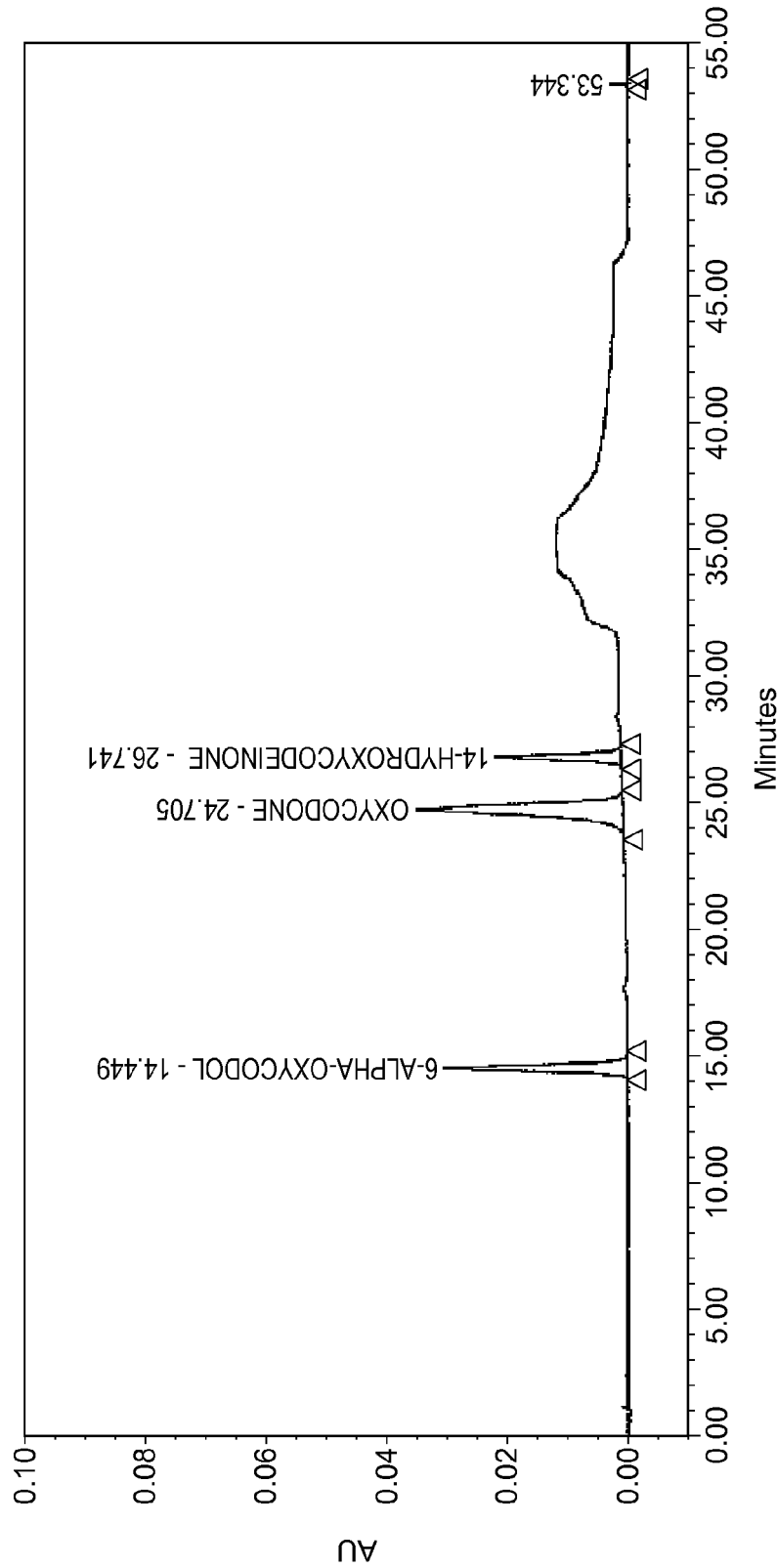
FIG. 3 illustrates a typical chromatogram of the retention time markers.
Figure 4:
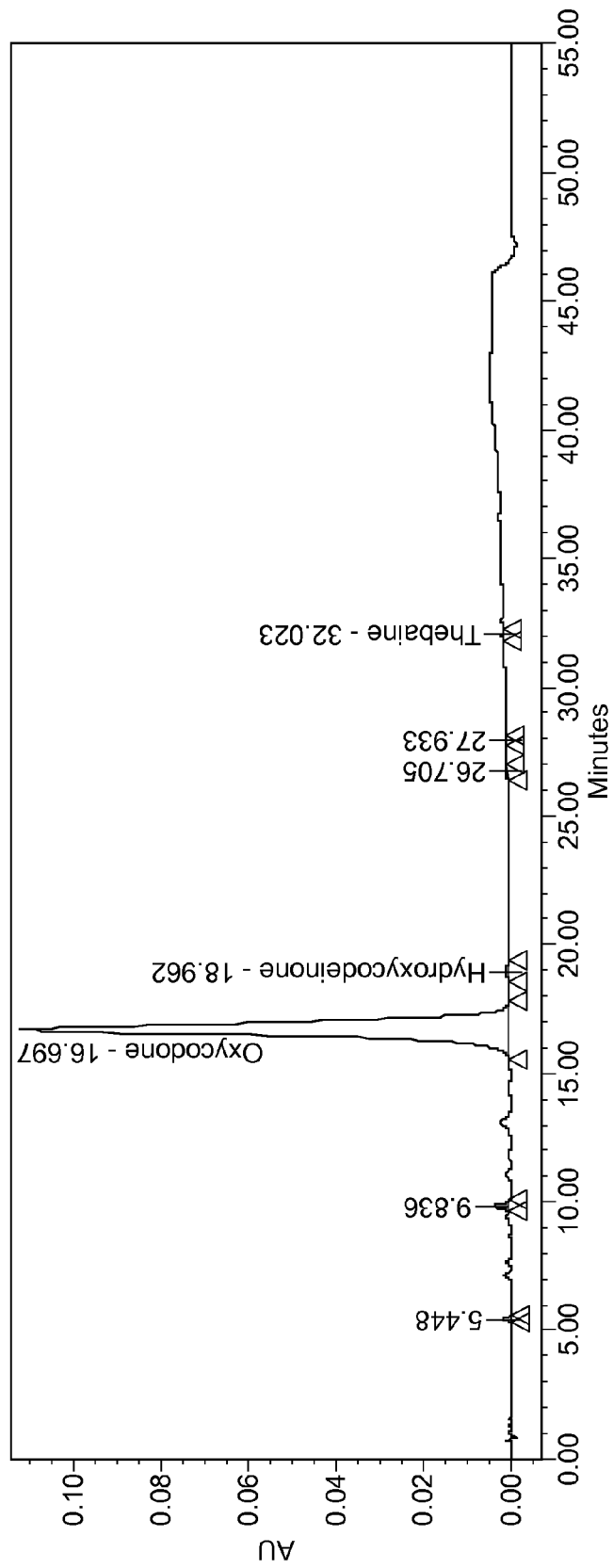
FIG. 4 illustrates a typical chromatogram of a sample solution.

Report the normalized percent, by area, of 14-Hydroxycodeinone from the sample injection to 0.01%. Report the percent, by area of 6α-Oxycodol from the sample injection to 0.01%.
2.13 Typical Chromatograms
FIG. 2 shows a typical chromatogram using 0.1N HCl/water acid solution as blank.
FIG. 3 shows a typical chromatogram of the retention time markers.
FIG. 4 shows a typical chromatogram of a sample solution.
3. UPLC/MS-SIM Method for PPM Level of 14-Hydroxycodeinone and Codeinone
3.1 Reagents and Materials:
(Equivalent reagents and materials may be substituted)

| | |
|---|---|
| Ammonium Acetate (NH$_4$OAc) | Fluka, HPLC Grade |
| Phosphoric Acid | EMD, HPLC Reagent |
| Methanol (MeOH) | Fisher Scientific, HPLC Grade |
| Acetonitrile (CAN) | Fisher Scientific, HPLC Grade |
| Purified Water (H$_2$O) | MilliQ, Model A10 Gradient Water System |
| 14-Hydroxycodeinone | JM Qualified Reference Standard |
| Codeinone | JM Qualified Reference Standard |

3.2 Instrumentation:
(Equivalent instrumentation can be used)

| | |
|---|---|
| UPLC | Waters Acquity UPLC System |
| MS Detector | Waters Acquity SQ Detector |
| UV Detector | Waters Acquity TUV Detector |
| Data System | Chromatography Data System, Current JM Version |
| Balance | Mettler-Toledo, Model AT261 or PG503-S, Delta Range |

3.3 Mobile Phase Preparation:
(For 1 L each, all containers need to be rinsed thoroughly in order to avoid unexpected peaks in the MS detection)
Mobile Phase A: Transfer 400 mL of deionized water into a suitable 1 L mobile phase container, weigh 0.77 g (±0.03 g) of Ammonium Acetate and transfer into the mobile phase container, shake and sonicate to dissolve completely. Transfer 25 mL of Acetonitrile, 25 mL of MeOH, and additional 550 mL of deionized water into the container, mix well and degas under vacuum for 10 min.
Mobile Phase B: Transfer 100 mL of deionized water into a suitable 1 L mobile phase container, weigh 0.77 g (±0.03 g) of Ammonium Acetate and transfer into the mobile phase container, shake and sonicate to dissolve completely. Transfer 450 mL of Acetonitrile and 450 mL of MeOH into the container, mix well and degas under vacuum for 10 min.
Diluent (1 L): Transfer 1 mL of H$_3$PO$_4$ into 1 L of deionized water and mix well.
3.4 Operating Conditions:

| LC Conditions | |
|---|---|
| Column | Waters, Acquity BEH Phenyl, 1.7 µm, 2.1 × 100 mm |
| Col. Temperature | 60° C. |
| Sample Temp | 15° C. |
| Injection Volume | 5 µL |
| Detection | UV at 210 nm |
| Flow Rate | 0.5 mL/min |
| Run Time | 10 min |

| Gradient Conditions | | | |
|---|---|---|---|
| Time (min) | % MP A | % MP B | Curve |
| initial | 80 | 20 | — |
| 4.5 | 80 | 20 | 6 |
| 4.6 | 0 | 100 | 6 |
| 8.0 | 0 | 100 | 6 |
| 8.1 | 80 | 20 | 6 |
| 10.0 | 80 | 20 | 6 |

| MS Conditions (ESI, Positive Mode) | |
|---|---|
| ESI Capillary Voltage | 2.5 kV |
| Cone Voltage | 30 V (Specify in Channel Table) |
| Extractor | 3 V |
| RF Lens | 0.1 V |
| Source Temperature | 150° C. |
| Desolvation Temperature | 450° C. |
| Desolvation Gas | 850 L/hr |
| Cone Gas | 30 L/hr |
| LM Resolution | 16.8 (Based on the annual calibration file) |
| HM Resolution | 15.0 (Based on the annual calibration file) |
| Ion Energy | 0.4 V (Based on the annual calibration file) |
| Gain | 1.0 |

-continued

| MS Conditions (ESI, Positive Mode) | |
|---|---|
| Mass Range (M + H⁺ in SIR Mode) | 298.25 (Codeinone) 314.24 (14-OH Codeinone) (Dalton, may vary slightly when the instrument is re-calibrated, set up two masses separately in two lines in MS Functions) |
| Mass Span | 0.4 (Dalton) |
| Dwell | 0.05 Sec |
| SIR Smoothing | Window Size: 2 Count: 1 |
| Scan Start Time | 1.0 min |
| Scan Stop Time | 6.0 min |
| Initial fluidic Settings in Events | FlowPath To Waste |

3.5 Approximate Retention Times of Known Analytes:

| Analyte | Approximate Retention Time (min) | RRT |
|---|---|---|
| Oxycodone | ~1.9 | 1.00 |
| 14-Hydroxycodeinone | ~2.6 | 1.37 |
| Codeinone | ~4.0 | 2.11 |

3.6 ABUK Working Standard Solution Preparation

Weigh 20 mg (±2 mg) each (accurate to the second digit passed the decimal point) of 14-Hydroxycodeinone and Codeinone reference standards into a 100 mL volumetric flask. Add ~20 mL of the diluent, vortex, sonicate with tapping to dissolve completely, dilute to volume with the diluent, and mix well. This is the ABUK stock solution-1.

Transfer 5.0 mL of the ABUK stock solution-1 into a 50 mL volumetric flask, dilute to volume with the diluent, and mix well. This is the ABUK stock solution-2.

Transfer 5.0 mL of the ABUK stock solution-2 into a 100 mL volumetric flask, dilute to volume with the diluent, and mix well. This is the ABUK stock solution-3.

Transfer 1.0 mL of the ABUK stock solution-3 into a 100 mL volumetric flask, dilute to volume with the diluent, and mix well. This is the ABUK working standard solution (~10 PPM). Keep all solutions at 15° C. or below if they are not immediately used. The solution stability will be determined in the validation.

3.7 Sensitivity Check Solution:

Transfer 1 mL of the ABUK working standard solution into a 10 mL volumetric flask, dilute to volume with the diluent, and mix well (~1 PPM). Keep the solution at 15° C. or below if it is not immediately used.

3.8 Sample Solution Preparation:

In duplicate, accurately weigh 55 mg (±5 mg) of the Oxycodone HCl sample into a 50 mL volumetric flask. Dissolve the sample and dilute to volume with the diluent. Mix well (Sonication may be necessary). Keep all solutions at 15° C. or below if they are not immediately used.

3.9 System Equilibration and Conditioning:

Pump Mobile Phase B for at least 10 minutes at a flow rate of 0.5 mL/min. Switch to Initial assay conditions and pump for at least 10 minutes.

3.10 Procedure:

Inject a sample solution once (any sample solution to be analyzed).

Determine the UV retention time that the peak of Oxycodone returns down to the baseline in the sample injection.

Inject the diluent twice.

Inject the sensitivity check solution once.

Inject six times of the ABUK working standard solution.

Ensure that the system suitability criteria are met.

Inject each sample solution in duplicate under the full gradient profile.

Inject two injections of the ABUK working standard solution as the standard check at the end of all sample injections.

Inject the diluent at the end.

Ensure that the results of the standard check are satisfied.

Quantify 14-Hydroxycodone and Codeinone in the sample(s) by comparing to the averaged response of the ABUK working standard solution.

Report the level of 14-OH Codeinone and Codeinone in the sample to the nearest 1 ppm.

3.11 System Suitability:

3.11.1 Sensitivity:

The peak heights of 14-Hydroxycodeinone and Codeinone in the sensitivity check solution must be NLT three (3) times the corresponding noise heights at the same retention time in the diluent injection (Noise level determination: the baseline of the diluent injection is integrated in three segments at the same retention time as the ABUK for a retention time window similar to the peak width of the ABUK in the sensitivity check solution. The noise level is the averaged peak height of the three segments).

3.11.2 Precision:

The % RSD of peak area responses, for both ABUKs, from six injections of the ABUK working standard solution, must be NMT 15.0%.

3.11.3 Standard Check:

The % difference between the averaged ABUK peak area (used as the denominator in the calculation) of the six working standard solution injections and the averaged corresponding ABUK peak area of the two standard check injections must be NMT 15.0%.

3.12 Calculations:

ABUK (PPM in Free Base Form):

$$PPM = \frac{(ABUK \text{ in Sample}^{AvgPA})(1000000)}{(ABUK \text{ STD}^{Conc.mg/mL})(ABUK \text{ Std Purity\{in decimal\}})}{(ABUK \text{ Std}^{Avg PA})(\text{Sample}^{Conc.mg/mL}) \times CF^*_{sample}}$$

Where:

| | |
|---|---|
| ABUK = | 14-Hydroxycodeinone or Codeinone |
| PA = | Peak Area |
| Std = | Standard |
| Avg = | Average |
| Conc = | Concentration (mg/mL) |
| CF = | Conversion Factor |

*Due to the fact that the reference standards of 14-OH Codeinone and Codeinone are in free base forms while the sample of Oxycodone is in HCl salt form, a conversion factor (CF) must be applied to the sample in the ppm calculation for the species form uniformity.

$$\text{Conversion Factor } (CF) = \frac{MW \text{ of the Base form}}{MW \text{ of the Salt form}}$$

| Analyte | Molecular Weight |
|---|---|
| Oxycodone | 315.36 |
| Oxycodone HCl | 351.82 |

3.13 Typical Chromatograms

Figure 5A:
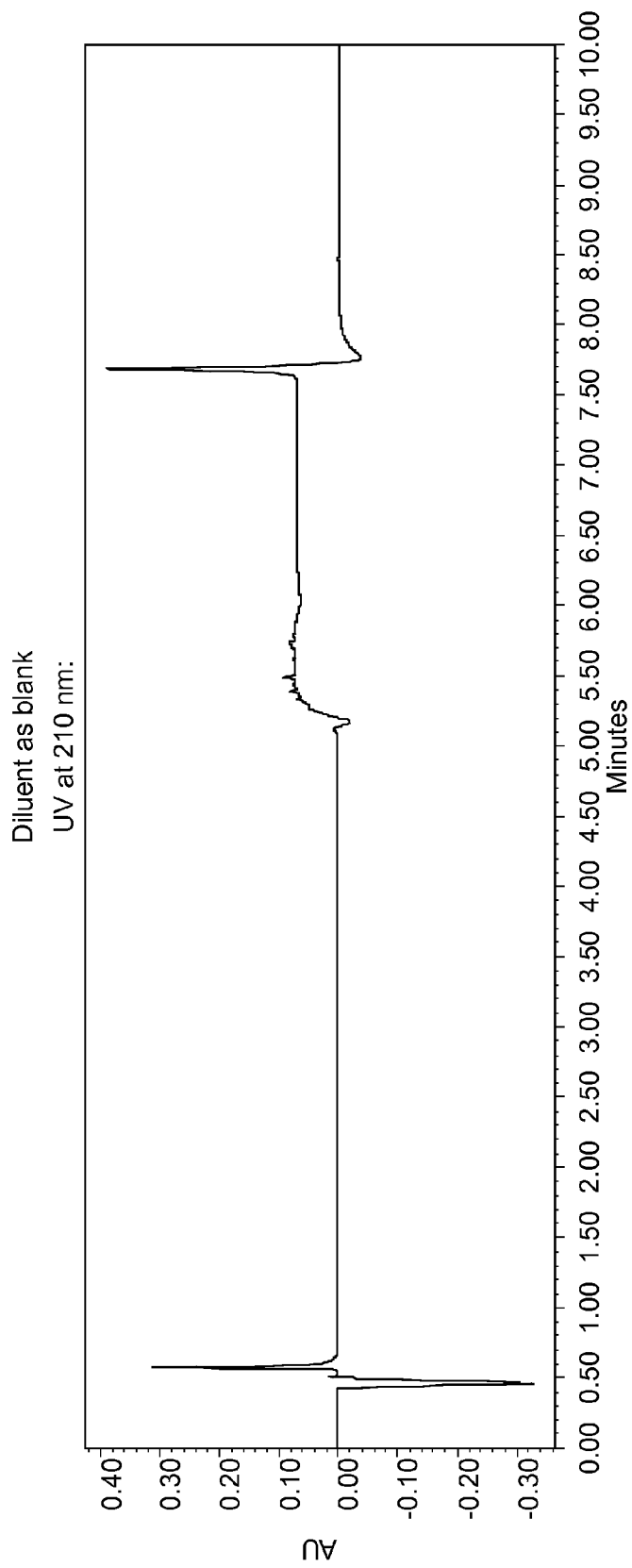
FIG. 5A illustrates a typical chromatogram of the diluent as blank (UV at 210 nm).
Figure 5B:
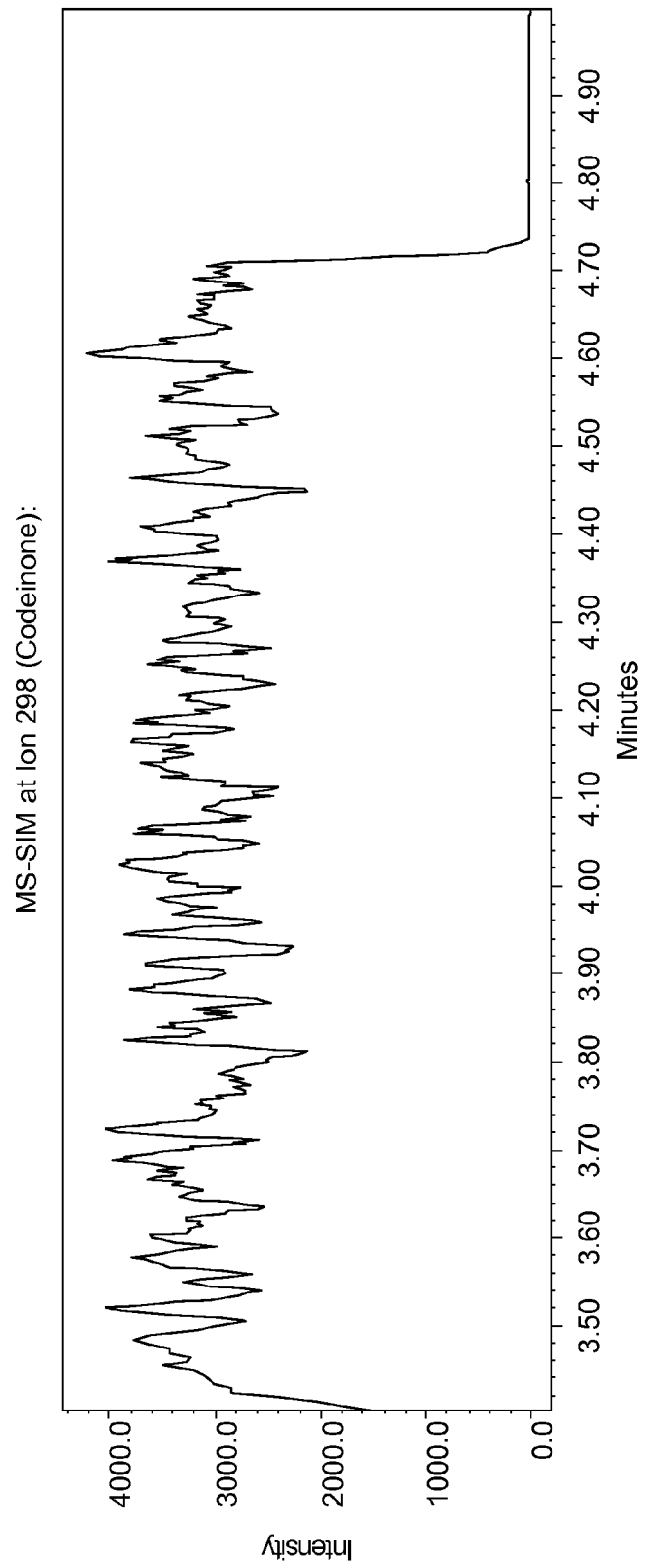
FIG. 5B illustrates a typical chromatogram of the diluent as blank (MS-SM at Ion 298 (Codeinone))
Figure 5C:
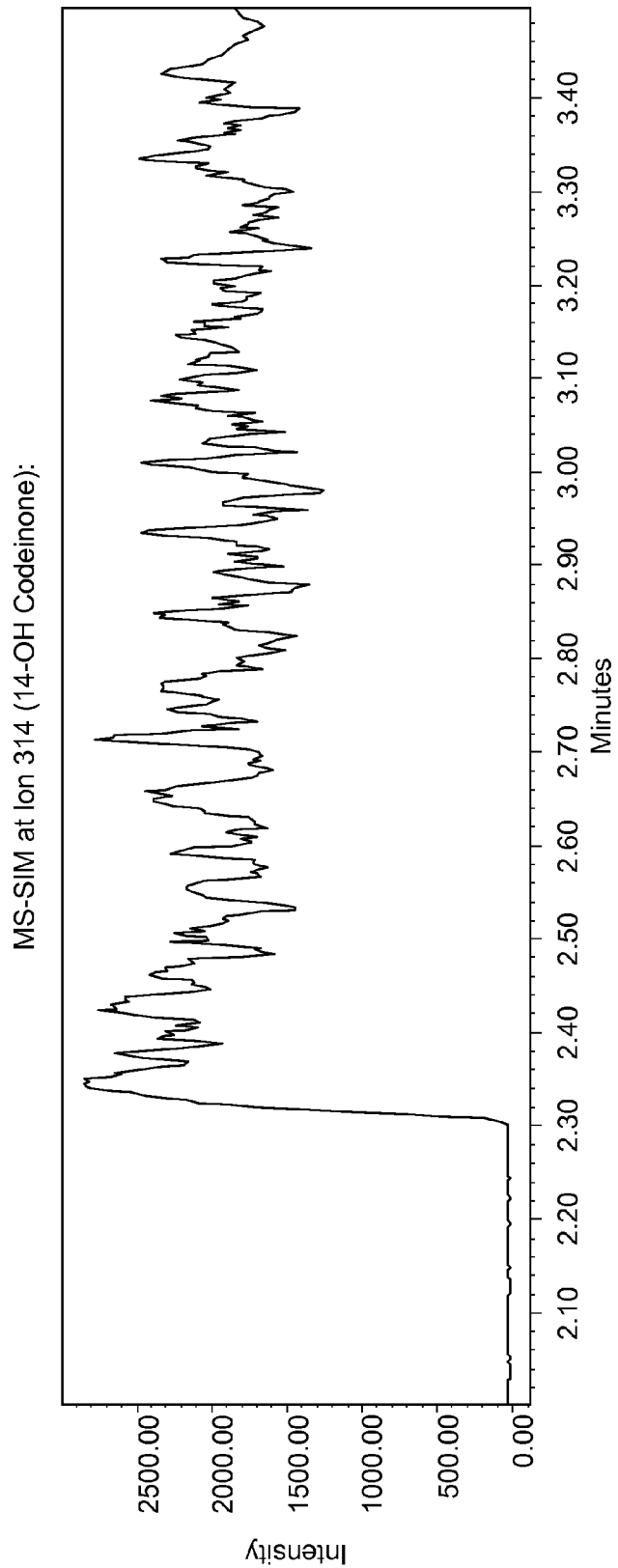
FIG. 5C illustrates a typical chromatogram of the diluent as blank (MS-SIM at ION 314 (14-OH Codeinone)).

FIG. 5 shows typical chromatograms of the diluent as blank.

Figure 6A:
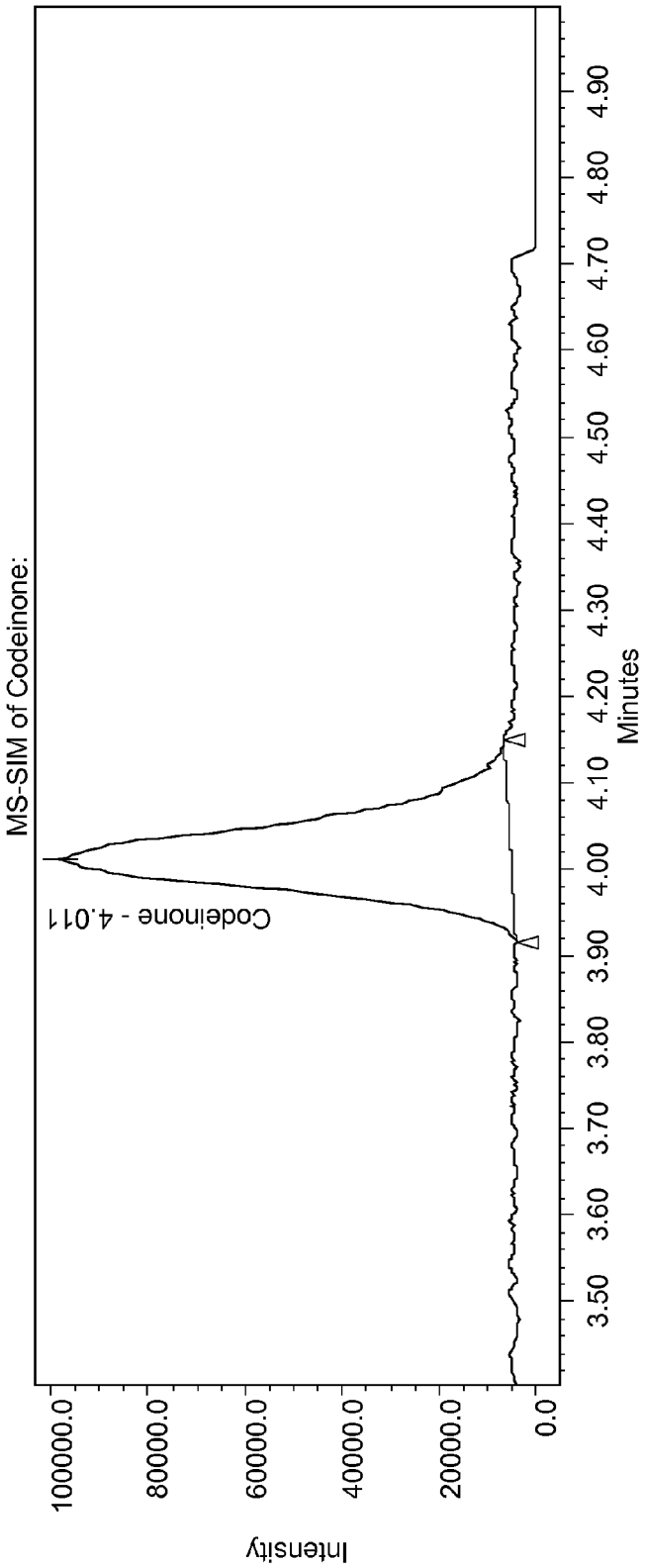
FIG. 6A illustrates a typical chromatogram of the ABUK Working Standard Solution (equivalent to 10 ppm) (MI-SIM (Codeinone)).
Figure 6B:
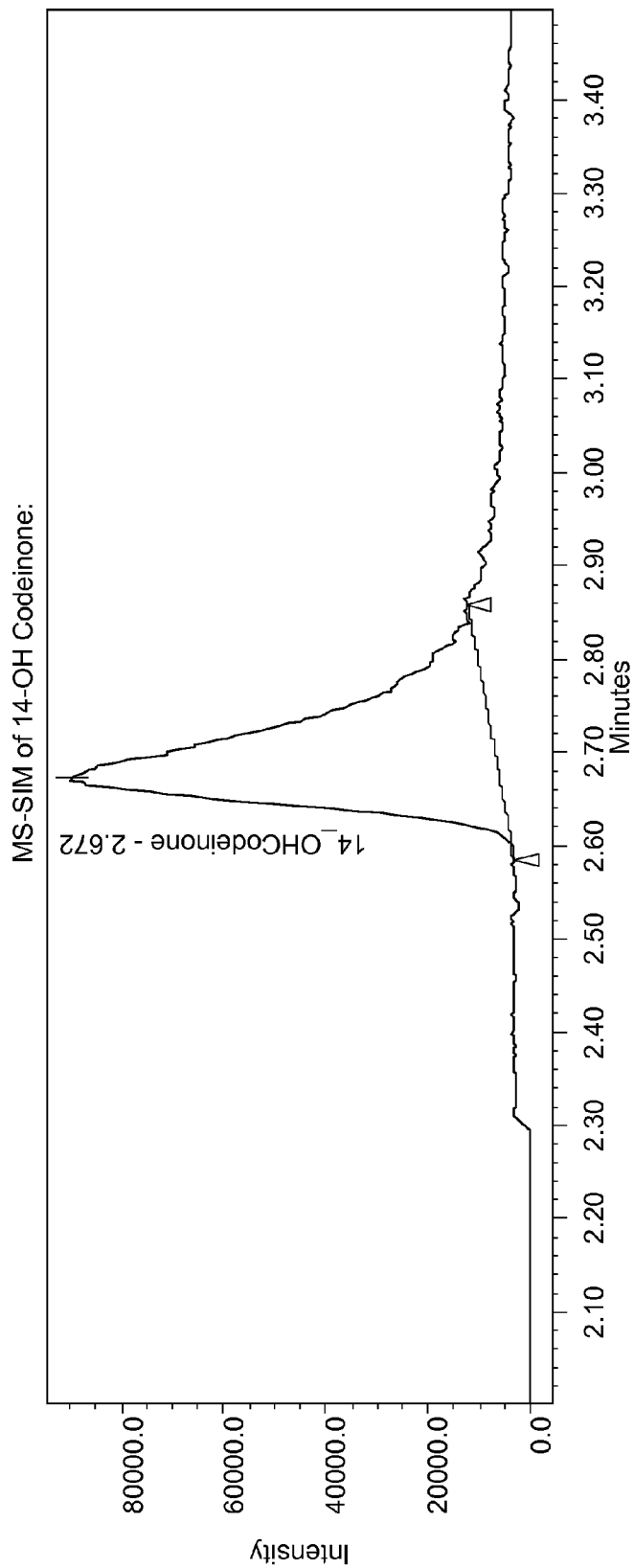
FIG. 6B illustrates a typical chromatogram of the ABUK Working Standard Solution (equivalent to 10 ppm) (MS-SIM (14-OH Codeinone)).

FIG. 6 shows typical chromatograms of the ABUK Working Standard Solution (equivalent to 10 ppm).

Figure 7A:
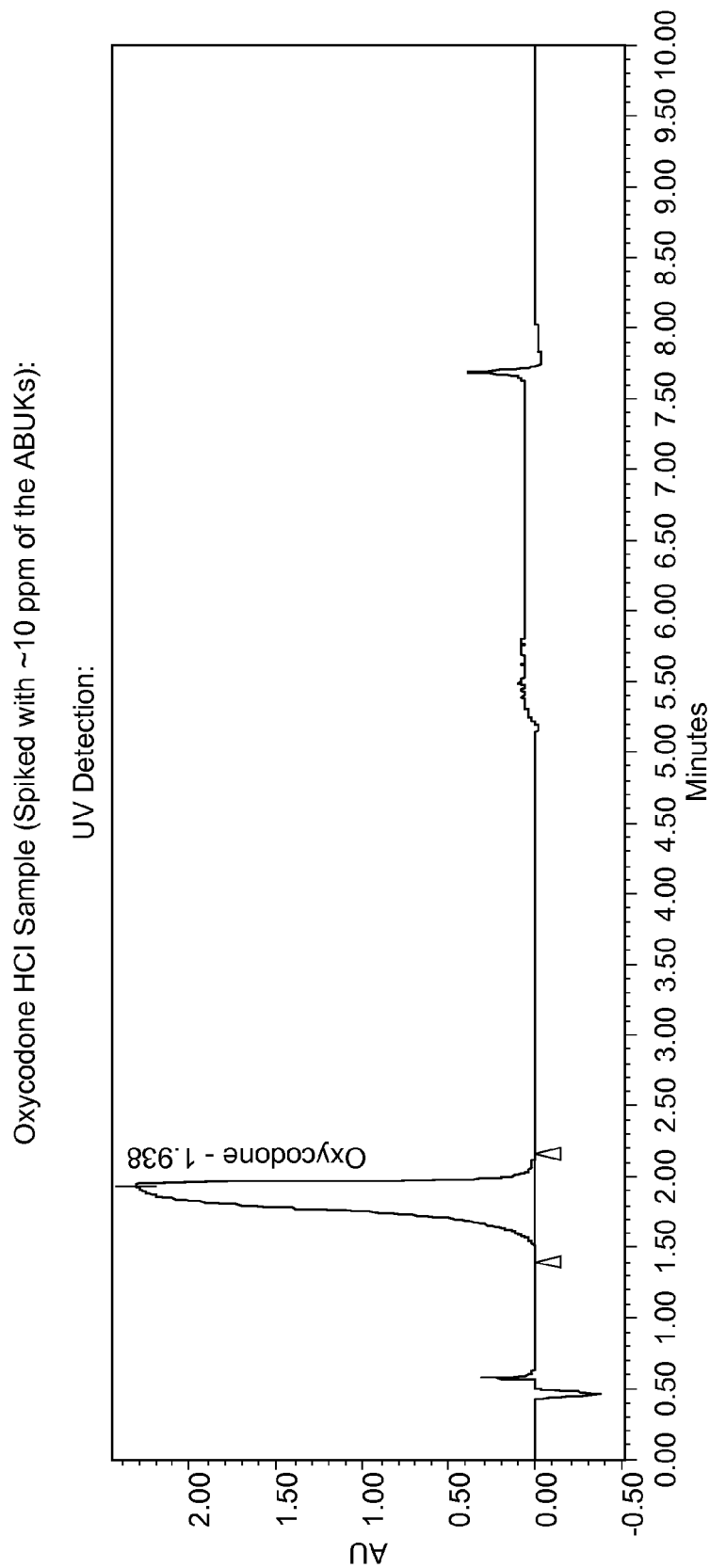
FIG. 7A illustrates a typical chromatogram of an Oxycodone HCl sample (spiked with ~10 ppm of the ABUKs) (UV Detection).
Figure 7B:
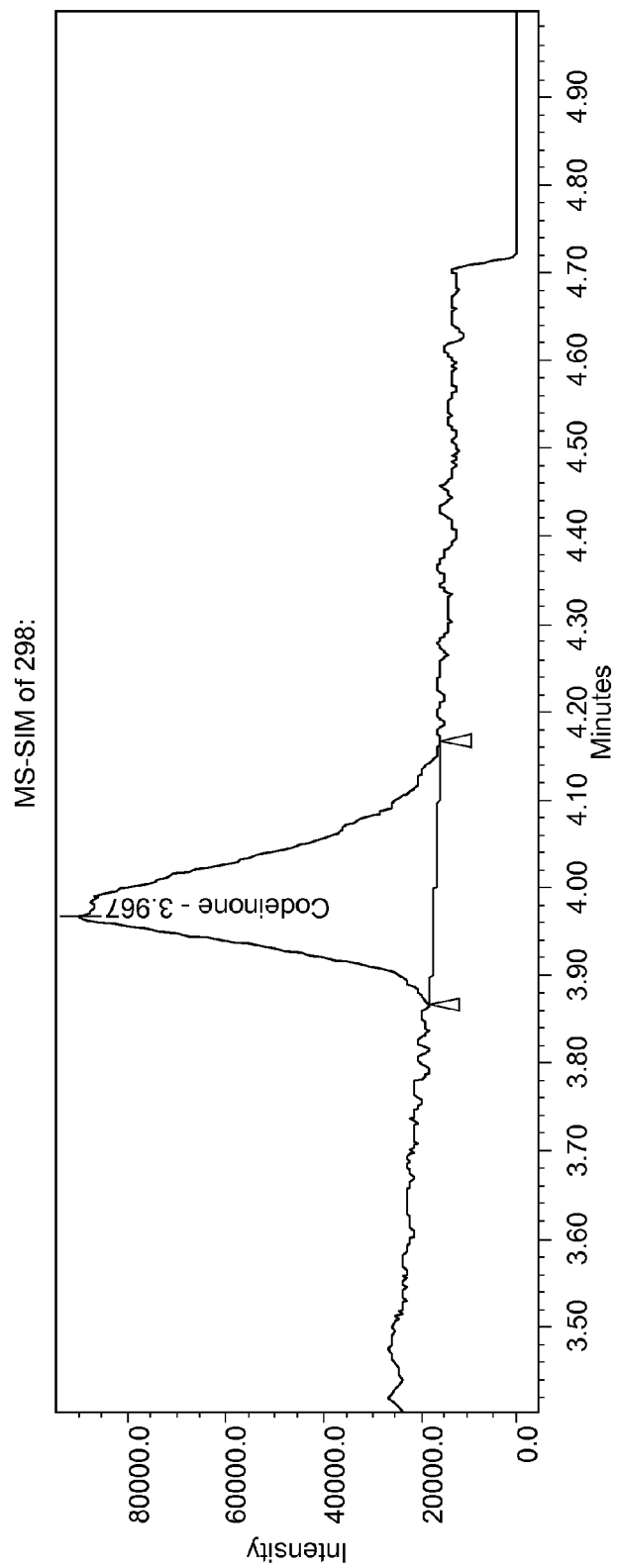
FIG. 7B illustrates a typical chromatogram of an Oxycodone HC sample (spiked with ~10 ppm of the ABUKs) (US-SIM of 298).
Figure 7C:
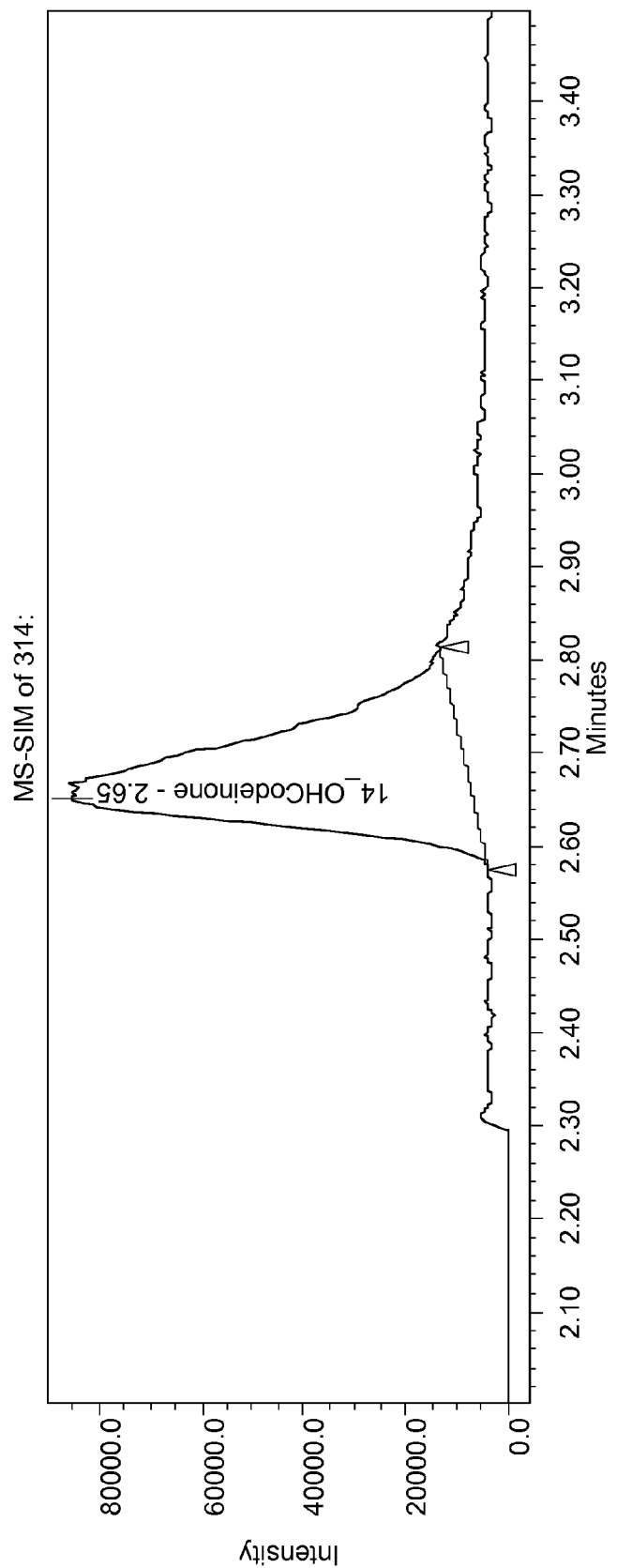
FIG. 7C illustrates a typical chromatogram of an Oxycodone HCl ample (spiked with ~10 ppm of the ABUKs) (US-SIM of 314).

FIG. 7 shows typical chromatograms of an Oxycodone HCl sample (spiked with ~10 ppm of the ABUKs).

Example 1 (Comparative)

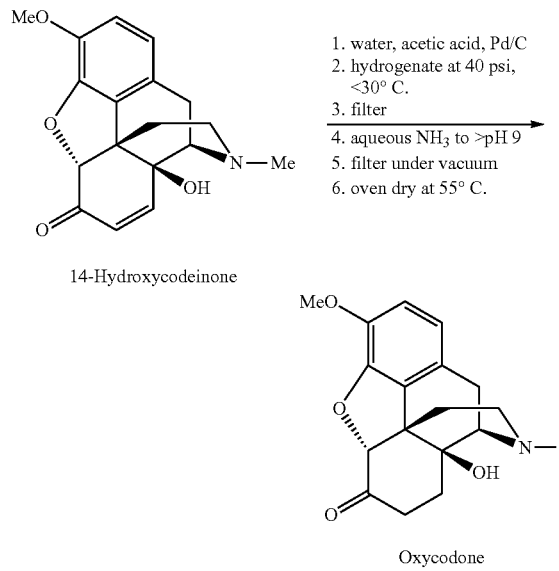

1. water, acetic acid, Pd/C
2. hydrogenate at 40 psi, <30° C.
3. filter
4. aqueous NH₃ to >pH 9
5. filter under vacuum
6. oven dry at 55° C.

14-Hydroxycodeinone

Oxycodone

A solution of acetic acid was prepared from 80% glacial acetic acid (18.3 mL) and water (96 mL).

Damp 14-hydroxycodeinone (51.0 g) was dissolved with the aid of sonication in the previously prepared dilute acetic acid. The brown 14-hydroxycodeinone solution had a volume of 156 mL and a pH of 3.93. This was divided into two lots (Example 1.1 and Example 1.2) of 78 mL which were then charged to separate Parr hydrogenation vessels with 10% palladium on charcoal (0.14 g×2 dry weight, LOD=58.25, 0.34 g×2 damp weight). The hydrogenation vessels were purged first with nitrogen/vacuum cycle (three times) and then with a hydrogen/vacuum cycle (three times). Example 1.1 and Example 1.2 were then each hydrogenated at 40 psi for two hours with the reaction flasks open to hydrogen reservoirs throughout the hydrogenation. It was observed that Example 1.2 was shaken at a greater rate than that of Example 1.1.

After two hours, the hydrogenation reactions were ceased and the excess hydrogen vented from the flasks. Each reaction mixture was then treated by filtering off the catalyst under suction on harbolite (5 mm layer) which was then washed with water (10 mL). Both filtrates were analysed by HPLC to determine the oxycodol and ABUK content (see Table 1). The filtrates of Example 1.1 and Example 1.2 were pH adjusted to pH 9.44 and pH 9.54 respectively over 30 mins using a 50:50 ammonia (0.88) and water solution. Fine cream coloured precipitates precipitated out of solution.

The mixtures were stirred for 2 hours within the temperature range of 5-10° C. on an ice and water bath. The precipitates were filtered off under suction and were washed with water (10 mL) and Alcohol M (10 mL). Alcohol M is 96% ethanol denaturated with 4% methanol. The precipitates were oven dried at 55° C. over 2 days before being powdered, weighed and analysed by HPLC (see Table 2) using the PhEur 6.0 Method. The yields of dry oxycodone alkaloid formed for Examples 1.1 and 1.2 were 13.9 g and 13.6 g respectively.

HPLC Analysis

The post hydrogenation liquors and isolated oxycodone alkaloids were analysed using the PhEur 6.0 HPLC method.

TABLE 1

A table of the HPLC data for the post hydrogenation liquor samples. Impurities with an area % of <0.01% have been omitted.

| | Example 1.1 Liquor (Slower agitation) | | | Example 1.2 Liquor (Faster agitation) | | |
|---|---|---|---|---|---|---|
| Substance | Retention Time (minutes) | Relative retention time | area % | Retention Time (minutes) | Relative retention time | area % |
| Unknown | 11.283 | 0.54 | 0.319 | 11.297 | 0.54 | 0.259 |
| Unknown | 12.978 | 0.62 | 0.076 | 12.967 | 0.62 | 0.054 |
| α-oxycodol | 13.268 | 0.64 | 1.815 | 13.287 | 0.64 | 1.178 |
| Unknown | 15.217 | 0.73 | 0.187 | 15.237 | 0.73 | 0.175 |
| DHDHC | 15.903 | 0.76 | 0.087 | 16.023 | 0.77 | 0.054 |
| β-oxycodol | 16.297 | 0.78 | 0.156 | 16.307 | 0.78 | 0.164 |
| Unknown | 18.160 | 0.87 | 0.282 | 18.19 | 0.87 | 0.188 |
| Oxycodone | 20.793 | 1.00 | 96.688 | 20.817 | 1.00 | 97.411 |
| Unknown | 24.015 | 1.15 | 0.389 | 24.053 | 1.16 | 0.516 |

DHDHC = 8,14-Dihydroxy-7,8-dihydrocodeinone

Table 1 summarises the results for the samples of the reaction liquors taken after hydrogenation. The 6α-oxycodol content in both samples were relatively high at 1.815 area % (Example 1.1) and 1.178 area % (Example 1.2).

TABLE 2

A table of the data for the isolated oxycodone alkaloid samples. Impurities with an area % of <0.01% have been omitted.

| Substance | Example 1.1 Dried product (Slower agitation) | | | Example 1.2 Dried product (Faster agitation) | | |
|---|---|---|---|---|---|---|
| | Retention Time (minutes) | Relative retention time | area % | Retention Time (minutes) | Relative retention time | area % |
| Unknown | 11.297 | 0.54 | 0.303 | 11.302 | 0.54 | 0.286 |
| α-oxycodol | 13.287 | 0.64 | 1.217 | 13.293 | 0.64 | 0.833 |
| Unknown | 13.910 | 0.67 | 0.34 | 13.923 | 0.67 | 0.030 |
| Unknown | 15.238 | 0.73 | 0.093 | 15.248 | 0.73 | 0.089 |
| β-oxycodol | 16.313 | 0.79 | 0.247 | 16.325 | 0.79 | 0.227 |
| Unknown | 18.190 | 0.88 | 0.185 | 18.207 | 0.88 | 0.152 |
| Oxycodone | 20.760 | 1.00 | 97.401 | 20.763 | 1.00 | 97.767 |
| Unknown | 24.057 | 1.16 | 0.467 | 24.082 | 1.16 | 0.559 |
| Unknown | 39.907 | 1.92 | 0.037 | 39.867 | 1.92 | 0.045 |
| Unknown | 46.880 | 2.26 | 0.016 | 46.897 | 2.26 | 0.012 |

Table 2 shows a difference in 6α-oxycodol content in the oxycodone alkaloid product when the reaction is agitated at a greater rate during the hydrogenation. The content of the 6β-oxycodol content, however, is higher at 0.247 area % (Example 1.1) and 0.227 area % (Example 1.2) in contrast to the hydrogenation liquors.

Example 2

A solution of acetic acid was prepared from 80% glacial acetic acid (18.3 mL) and water (96 mL).

Damp 14-hydroxycodeinone (51.0 g) was dissolved with the aid of sonication in the previously prepared dilute acetic acid. The brown 14-hydroxycodeinone solution had a volume of 153 mL. This was divided into two lots of 76.5 mL and reacted further as described below in Example 2.1 and Example 2.2.

Example 2.1 (According to the Invention)

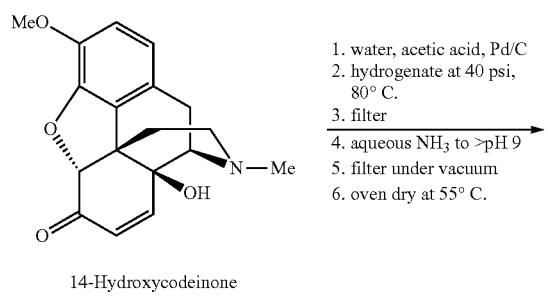

1. water, acetic acid, Pd/C
2. hydrogenate at 40 psi, 80° C.
3. filter
4. aqueous NH₃ to >pH 9
5. filter under vacuum
6. oven dry at 55° C.

14-Hydroxycodeinone

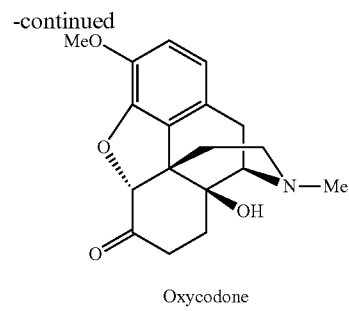

Oxycodone

The solution of 14-hydroxycodeinone in dilute acetic acid was charged to a Parr hydrogenation vessel with 10% palladium on charcoal (0.14 g dry weight, LOD=58.25, 0.34 g damp weight). The hydrogenation vessel was then placed in a heating jacket on a Parr hydrogenator. The vessel was then purged with a nitrogen/vacuum cycle (three times) and followed by a hydrogen/vacuum cycle (three times). After the final purge cycle the vessel was left under vacuum and was shaken whilst the vessel was heated to 80° C. Hydrogen was reintroduced into the vessel at a pressure of 40 psi once 80° C. had been attained. The hydrogenation was carried out for 2 hours maintaining the temperature at 80° C. with the reaction flask open to the reservoir tank.

After 2 hours the pressure in the hydrogen vessel had reduced to 37 psi. The hydrogen was vented. The Pd/C catalyst was filtered off on harbolite (5 mm layer on filter paper) and was washed with water (10 mL). The filtrate was analysed by HPLC to determine the oxycodol content (see Table 3). The bulk of the filtrate was left overnight after which it was pH adjusted to pH 9.41 over 30 mins using a 50:50 ammonia (0.88) and water solution. A fine cream coloured precipitate precipitated out of solution.

The mixture was stirred for 2 hours within the temperature range of 5-10° C. on an ice and water bath. The precipitate was filtered off under suction and was washed with water (10 mL) and alcohol M (10 mL). The precipitate was oven dried at 55° C. overnight before being powdered, weighed and analysed by HPLC (see Table 4). 12.3 g of dry oxycodone alkaloid was obtained.

HPLC Analysis

The post hydrogenation liquor and isolated oxycodone alkaloid of Example 2.1 were analysed using the PhEur 6.0 HPLC method.

TABLE 3

A table of the HPLC data for the post hydrogenation liquor.
Impurities with an area % of <0.01% have been omitted.

| Substance | Retention Time (minutes) | Relative retention time (minutes) | area % |
|---|---|---|---|
| Unknown | 11.365 | 0.54 | 0.367 |
| Unknown | 12.225 | 0.58 | 0.019 |
| Unknown | 12.995 | 0.62 | 0.164 |
| α-oxycodol | 13.403 | 0.64 | 0.170 |
| Unknown | 14.093 | 0.67 | 0.056 |
| Unknown | 15.383 | 0.73 | 0.244 |
| β-oxycodol + DHDHC | 16.472 | 0.79 | 0.292 |
| Unknown | 18.337 | 0.88 | 0.394 |
| Oxycodone | 20.952 | 1.00 | 97.672 |
| Unknown | 22.245 | 1.06 | 0.114 |
| Unknown | 23.897 | 1.14 | 0.322 |
| Codeinone | 25.060 | 1.20 | 0.069 |
| Unknown | 39.890 | 1.90 | 0.070 |
| Unknown | 46.853 | 2.24 | 0.029 |

DHDHC = 8,14-Dihydroxy-7,8-dihydrocodeinone

Table 3 shows that the 6α-oxycodol content is considerably lower at 0.170% than that seen in the reaction liquor from Example 1.1 which had a level of 1.82%. As both samples were hydrogenated on the same Parr hydrogenator, the analysis of the sample obtained from the present Example conducted under hot hydrogenation conditions showed a large reduction in the amount of 6α-oxycodol being formed.

TABLE 4

A table of the data for the isolated oxycodone alkaloid.
Impurities with an area % of <0.01% have been omitted.

| Substance | Retention Time (minutes) | Relative retention time (minutes) | area % |
|---|---|---|---|
| Unknown | 7.348 | 0.37 | 0.021 |
| Unknown | 9.417 | 0.48 | 0.018 |
| Unknown | 10.612 | 0.54 | 0.307 |
| Unknown | 12.157 | 0.62 | 0.155 |
| α-oxycodol | 12.435 | 0.63 | 0.088 |
| Unknown | 13.105 | 0.67 | 0.038 |
| Unknown | 14.353 | 0.73 | 0.103 |
| β-oxycodol + DHDHC | 15.382 | 0.78 | 0.247 |
| Unknown | 17.138 | 0.87 | 0.183 |
| Oxycodone | 19.643 | 1.00 | 98.451 |
| Unknown | 22.612 | 1.15 | 0.237 |
| Unknown | 29.510 | 1.50 | 0.011 |
| Unknown | 32.707 | 1.67 | 0.010 |
| Unknown | 38.470 | 1.96 | 0.079 |
| Unknown | 45.472 | 2.31 | 0.029 |

DHDHC = 8,14-Dihydroxy-7,8-dihydrocodeinone

The analysis of the isolated oxycodone alkaloid showed a further reduction in the amount of 6α-oxycodol from 0.170% in Table 3 to 0.088% in Table 4.

The heating of the hydrogenation vessel throughout the hydrogenation had beneficially reduced the amount of 6α-oxycodol formed during the hydrogenation of 14-hydroxycodeinone to oxycodone alkaloid. The HPLC analysis showed that 6α-oxycodol formation had been significantly reduced in the present experiment in comparison with Example 1.1.

Example 2.2 (Comparative)

Reduction in Hydrogen Pressure

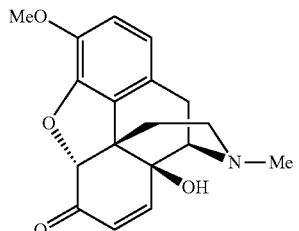

14-Hydroxycodeinone 1. water, acetic acid, Pd/C
2. hydrogenate at 12 psi, <30° C.
3. filter
4. aqueous NH₃ to >pH 9
5. filter under vacuum
6. oven dry at 55° C.

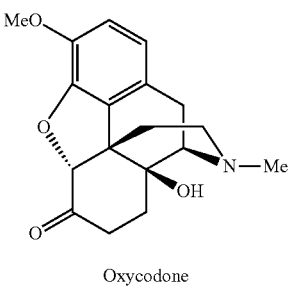

Oxycodone

The solution of 14-hydroxycodeinone in dilute acetic acid was charged to a Parr hydrogenation vessel with 10% palladium on charcoal (0.14 g dry weight, LOD=58.25, 0.34 g damp weight). The vessel was then placed on the Parr hydrogenator. The vessel was then purged with a nitrogen/vacuum cycle (three times) and followed by a hydrogen/vacuum cycle (three times). After the final purge cycle hydrogen was reintroduced into the vessel and the pressure was reduced to 12±5 psi. The hydrogenation was carried out for 2 hours at an ambient temperature with the reaction flask open to the reservoir tank.

The hydrogen was vented. The Pd/C catalyst was filtered off on harbolite (5 mm layer on filter paper) and was washed with water (10 mL). The filtrate was analysed by HPLC to determine the oxycodol content (see Table 5). The bulk of the filtrate was left overnight after which it was pH adjusted to pH 9.33 over 30 mins using a 50:50 ammonia (0.88) and water solution. A fine cream coloured precipitate precipitated out of solution.

The mixture was stirred for 2 hours within the temperature range of 5-10° C. on an ice and water bath. The precipitate was filtered off under suction and was washed with water (10 mL) and alcohol M (10 mL). The precipitate was oven dried at 55° C. overnight before being powdered, weighed and analysed by HPLC (see Table 6). 13.7 g of dry oxycodone alkaloid was obtained.

HPLC Analysis

The post hydrogenation liquor and isolated oxycodone alkaloid of Example 2.2 were analysed using the PhEur 6.0 HPLC method.

TABLE 5

A table of the HPLC data for the post hydrogenation liquor.
Impurities with an area % of <0.01% have been omitted.

| Substance | Retention time (minutes) | Relative retention time (minutes) | area % |
| --- | --- | --- | --- |
| Unknown | 11.310 | 0.54 | 0.370 |
| α-oxycodol | 13.298 | 0.64 | 2.726 |
| Unknown | 14.690 | 0.71 | 0.023 |
| Unknown | 15.257 | 0.73 | 0.152 |
| DHDHC | 15.917 | 0.76 | 0.134 |
| β-oxycodol | 16.337 | 0.78 | 0.175 |
| Unknown | 18.197 | 0.87 | 0.894 |
| Oxycodone | 20.825 | 1.00 | 95.210 |
| Unknown | 23.817 | 1.14 | 0.215 |
| Codeinone | 24.952 | 1.20 | 0.026 |
| Unknown | 39.883 | 1.92 | 0.045 |
| Unknown | 46.817 | 2.25 | 0.030 |

DHDHC = 8,14-Dihydroxy-7,8-dihydrocodeinone

The 6α-oxycodol content of the present experiment is greater (at 2.726%) than that seen in the reaction liquor of Example 1.2 (1.178%). Both samples were hydrogenated on the same Parr hydrogenator so analysis of the post low pressure hydrogenation liquors shows a greater amount of 6α-oxycodol being formed.

TABLE 6

A table of the data for the isolated oxycodone alkaloid.
Impurities with an area % of <0.01% have been omitted.

| Substance | Retention Time (minutes) | Relative retention time (minutes) | area % |
| --- | --- | --- | --- |
| Unknown | 7.350 | 0.37 | 0.015 |
| Unknown | 9.408 | 0.48 | 0.016 |
| Unknown | 10.617 | 0.54 | 0.306 |
| α-oxycodol | 12.450 | 0.63 | 1.662 |
| Unknown | 13.083 | 0.67 | 0.035 |
| Unknown | 14.353 | 0.73 | 0.081 |
| DHDHC | 14.937 | 0.76 | 0.091 |
| β-oxycodol | 15.382 | 0.78 | 0.174 |
| Unknown | 17.137 | 0.87 | 0.319 |
| Oxycodone | 19.655 | 1.00 | 96.750 |
| Unknown | 22.893 | 1.16 | 0.448 |
| Unknown | 29.542 | 1.50 | 0.010 |
| Unknown | 38.570 | 1.96 | 0.062 |
| Unknown | 45.487 | 2.31 | 0.018 |

DHDHC = 8,14-Dihydroxy-7,8-dihydrocodeinone

The amount of 6α-oxycodol in the isolated oxycodone alkaloid of the present experiment is approximately double that observed in the isolated oxycodone alkaloid of Example 1.2. The amounts of 6β-oxycodol in both are approximately similar.

Example 3 (Comparative)

Increased Catalyst Loading

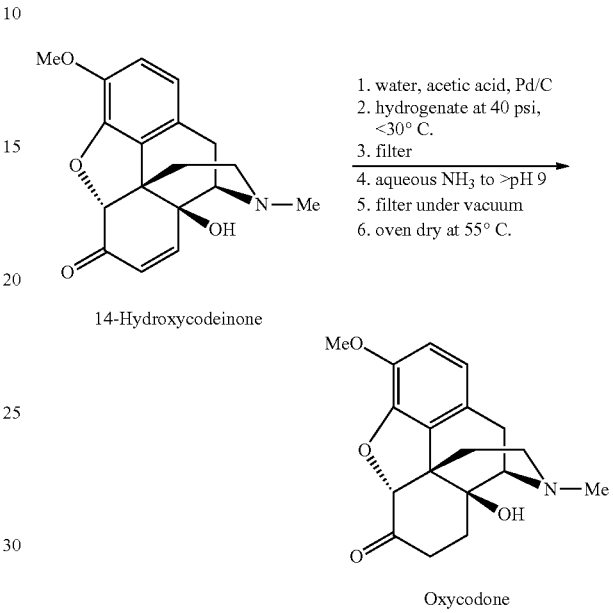

1. water, acetic acid, Pd/C
2. hydrogenate at 40 psi, <30° C.
3. filter
4. aqueous NH₃ to >pH 9
5. filter under vacuum
6. oven dry at 55° C.

14-Hydroxycodeinone

Oxycodone

A solution of acetic acid was prepared from 80% glacial acetic acid (9.2 mL) and water (48 mL).

Damp 14-hydroxycodeinone (25.5 g) was dissolved with the aid of sonication in the previously prepared dilute acetic acid. The brown 14-hydroxycodeinone solution had a volume of 76 mL.

The solution of 14-hydroxycodeinone in dilute acetic acid was charged to a Parr hydrogenation vessel with 10% palladium on charcoal (0.29 g dry weight, LOD=58.25, 0.70 g damp weight). The vessel was then put on a Parr hydrogenator. The vessel was then purged with a nitrogen/vacuum cycle (three times) and followed by a hydrogen/vacuum cycle (three times). After the final purge cycle the vessel hydrogen was reintroduced into the vessel and the pressure of hydrogen was set to 40±5 psi. The hydrogenation was carried out for 2.5 hours at an ambient temperature with the reaction flask open to the reservoir tank.

After this time, the hydrogen was vented. The Pd/C catalyst was filtered off on harbolite (5 mm layer on filter paper) and was washed with water (10 mL). The filtrate was analysed by HPLC to determine the oxycodol content (see Table 7). The bulk of the filtrate was left overnight after which it was pH adjusted to pH 9.33 over 30 mins using a 50:50 ammonia (0.88) and water solution. A fine cream coloured precipitate precipitated out of solution.

The mixture was stirred for 2 hours within the temperature range of 5-10° C. on an ice and water bath. The precipitate was filtered off under suction and was washed with water (10 mL) and alcohol M (10 mL). The precipitate was oven dried at 55° C. overnight before being powdered, weighed and analysed by HPLC (see Table 8). 12.9 g of dry oxycodone alkaloid was obtained.

HPLC Analysis

The post hydrogenation liquor and isolated oxycodone alkaloid samples were analysed using the PhEur 6.0 HPLC method.

TABLE 7

A table of the HPLC data for the post hydrogenation liquor.
Impurities with an area % of <0.01% have been omitted.

| Substance | Retention Time (minutes) | Relative retention time (minutes) | area % |
| --- | --- | --- | --- |
| Unknown | 10.630 | 0.54 | 0.373 |
| α-oxycodol | 12.485 | 0.63 | 2.277 |
| Unknown | 14.388 | 0.73 | 0.136 |
| DHDHC | 14.965 | 0.76 | 0.132 |
| β-oxycodol | 15.417 | 0.78 | 0.151 |
| Unknown | 17.177 | 0.87 | 0.769 |
| Oxycodone | 19.747 | 1.00 | 95.960 |
| Unknown | 22.660 | 1.15 | 0.203 |

DHDHC = 8,14-Dihydroxy-7,8-dihydrocodeinone

TABLE 8

A table of the data for the isolated oxycodone alkaloid.
Impurities with an area % of <0.01% have been omitted.

| Substance | Retention Time (minutes) | Relative retention time (minutes) | area % |
| --- | --- | --- | --- |
| Unknown | 11.005 | 0.54 | 0.295 |
| α-oxycodol | 12.940 | 0.64 | 1.688 |
| Unknown | 13.553 | 0.67 | 0.029 |
| Unknown | 14.480 | 0.71 | 0.058 |
| Unknown | 14.885 | 0.73 | 0.080 |
| DHDHC | 15.510 | 0.76 | 0.143 |
| β-oxycodol | 15.940 | 0.78 | 0.145 |
| Unknown | 17.803 | 0.88 | 0.129 |
| Oxycodone | 20.335 | 1.00 | 97.132 |
| Unknown | 23.583 | 1.16 | 0.292 |

DHDHC = 8,14-Dihydroxy-7,8-dihydrocodeinone

The 6α-oxycodol content of these samples is high at 2.277% in the post hydrogenation liquors and 1.688% in the isolated oxycodone alkaloid. The samples produced also have a larger 6α-oxycodol content than in the corresponding samples in Example 1.1 (where the same hydrogenator was used). Example 1.1 has respective 6α-oxycodol contents of 1.815% and 1.217% and so there is ~20% more 6α-oxycodol in samples of the present experiment. 6β-Oxycodol was observed to be approximately the same in Example 1.1 and the present experiment.

Doubling the catalyst load therefore increased the amount of 6α-oxycodol observed by HPLC analysis by ~20%.

Example 4 (Comparative)

Pretreatment of Catalyst/Acid Mixture

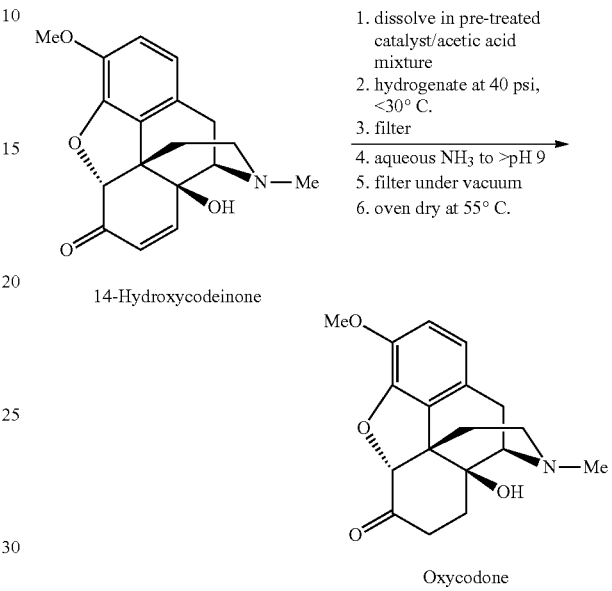

14-Hydroxycodeinone 1. dissolve in pre-treated catalyst/acetic acid mixture
2. hydrogenate at 40 psi, <30° C.
3. filter
4. aqueous NH$_3$ to >pH 9
5. filter under vacuum
6. oven dry at 55° C.

Oxycodone

A solution of acetic acid was prepared from 80% glacial acetic acid (9.2 mL) and water (48 mL).

10% Pd/C (0.14 g dry weight, LOD=58.25, 0.34 g damp weight) was charged to a Parr hydrogenation vessel with the above dilute acetic acid solution. This was placed on the same Parr hydrogenator as used in Example 1.2 and three nitrogen/vacuum purge cycles were performed followed by three hydrogen/vacuum cycles. After the final cycle, the hydrogenation vessel was put under vacuum and the flask was heated to 80±5° C. whilst being shaken. Hydrogen was reintroduced to the vessel once 80° C. had been attained at a pressure of 40±5 psi and the flask was shaken under a hydrogen pressure at 80±5° C. for 2 hours. The vessel was then allowed to cool to ambient temperature without agitation before damp 14-hydroxycodeinone (25.5 g) was dissolved in the acetic acid/Pd catalyst mixture with the aid of sonication. The vessel was then placed back on the Parr hydrogenator and three nitrogen/vacuum purge cycles were performed followed by three hydrogen/vacuum cycles. After the final cycle, the hydrogenation vessel was filled with hydrogen to a pressure of 40±5 psi and the hydrogenation was carried out over two hours with agitation at an ambient temperature (below 30° C.). The reaction vessel was open to the hydrogen reservoir throughout the hydrogenation.

After this time, the hydrogen was vented. The Pd/C catalyst was filtered off on harbolite (5 mm layer on filter paper) and was washed with water (10 mL). The filtrate was analysed by HPLC to determine the oxycodol content (see Table 9). The bulk of the filtrate was left overnight after which it was pH adjusted to pH 9.42 over 30 mins using a 50:50 ammonia (0.88) and water solution. A fine cream coloured precipitate precipitated out of solution.

The mixture was stirred for 2 hours within the temperature range of 5-10° C. on an ice and water bath. The precipitate was filtered off under suction and was washed with water (10 mL) and alcohol M (10 mL). The precipitate was oven dried at 55° C. overnight before being powdered, weighed and analysed by HPLC (see Table 10) using the PhEur 6.0 Method. 13.7 g of dry oxycodone alkaloid was obtained.

HPLC Analysis

The post hydrogenation liquor and isolated oxycodone alkaloid samples were analysed using the PhEur 6.0 HPLC.

TABLE 9

A table of the HPLC data for the post hydrogenation liquor. Impurities with an area % of <0.01% have been omitted.

| Substance | Retention Time (minutes) | Relative retention time (minutes) | area % |
|---|---|---|---|
| Unknown | 10.640 | 0.54 | 0.363 |
| α-oxycodol | 12.495 | 0.63 | 2.625 |
| Unknown | 14.398 | 0.73 | 0.086 |
| DHDHC | 14.977 | 0.76 | 0.151 |
| β-oxycodol | 15.427 | 0.78 | 0.148 |
| Unknown | 17.205 | 0.87 | 0.275 |
| Oxycodone | 19.975 | 1.00 | 96.085 |
| Unknown | 20.975 | 1.06 | 0.052 |
| Unknown | 22.697 | 1.15 | 0.214 |

DHDHC = 8,14-Dihydroxy-7,8-dihydrocodeinone

TABLE 10

A table of the data for the isolated oxycodone alkaloid. Impurities with an area % of <0.01% have been omitted.

| Substance | Retention Time (minutes) | Relative retention time (minutes) | area % |
|---|---|---|---|
| Unknown | 11.010 | 0.54 | 0.302 |
| α-oxycodol | 12.947 | 0.64 | 1.436 |
| Unknown | 13.585 | 0.67 | 0.034 |
| Unknown | 14.903 | 0.73 | 0.072 |
| DHDHC | 15.525 | 0.76 | 0.121 |
| β-oxycodol | 15.957 | 0.78 | 0.160 |
| Unknown | 17.805 | 0.88 | 0.272 |
| Oxycodone | 20.340 | 1.00 | 97.361 |
| Unknown | 23.567 | 1.16 | 0.242 |

DHDHC = 8,14-Dihydroxy-7,8-dihydrocodeinone

The present experiment was hydrogenated using the same Parr hydrogenator as in Example 1.2 and so the HPLC results of the present example will be compared with those of Example 1.2. The amount of 6α-oxycodol increased in this experiment relative to the levels seen in Example 1.2 which had the same hydrogenation conditions except for the prehydrogenation priming of the catalyst in the present experiment. In this regard, Example 1.2 had 6α-oxycodol levels of 1.178% and 0.833% respectively. The present experiment had 6α-oxycodol levels of 2.625% and 1.436% respectively which is ~100% greater than in Example 1.2. The levels of 6β-oxycodol in Example 1.2 and the present experiment were approximately equal at ca. 0.2%.

Example 5 (According to the Invention)

Evaluation of the Effects of Temperature with No Hold Time Before Addition of Hydrogen 14-Hydroxycodeinone (100 g, LOD 50.9%) was added to a hastalloy hydrogenation vessel, together with water (145.5 mL) and 80% acetic acid solution (24.0 mL). The mixture was stirred until the majority of the 14-hydroxycodeinone was in solution. 10% Pd/C (1.02 g) was added and it was observed that some mild effervescence occurred. As the 14-hydroxycodeinone was very damp on weighing, it was considered possible that some ammonium formate was present (generated during the preparation of the 14-hydroxycodeinone) which, on addition of acid, formed formic acid. The formic acid may have then formed hydrogen gas in the presence of the catalyst.

Once the effervescence had subsided a little, the flask was evacuated and purged with nitrogen four times then released to ambient pressure before sealing (under nitrogen). The stirrer was started and the reaction mixture heated to 80° C. The pressure increased on heating and hydrogen was added as soon as the mixture reached 80° C. The hydrogen pressure was monitored until stable. To monitor uptake, the flask was isolated and the pressure of the reaction flask headspace monitored. No decrease in pressure indicated that the hydrogenation had ceased. Once the hydrogen pressure was stable, the flask was isolated from the hydrogen supply and left under a hydrogen atmosphere at 80° C. overnight.

| Time | Flask gauge/psi | Temp/° C. | Notes |
|---|---|---|---|
| 0 | 0 | 18 | Heating started |
| 20 min | 19 | 89 | Reaction mixture allowed to cool to 84° C. before pressurising with hydrogen |
| 29 min | 41 | 84 | Hydrogenated initially with flask isolated from hydrogen supply |
| 31 min | 31 | | Pressurised back to 41 psi then left open to hydrogen supply |
| 44 min | 43 | | Hydrogen uptake monitored - still consuming |
| 56 min | 43 | 83 | Hydrogen uptake monitored - not consuming. Left isolated from hydrogen supply. |
| 76 min | 41 | 75 | |
| 16 h 5 min | 41 | 80 | |
| 17 h 20 min | 41 | 80 | Heat removed |

The reaction mixture was allowed to cool to less than 30° C. with the aid of an ice bath. Hydrogen was released to vacuum and the flask purged with a vacuum/nitrogen cycle. The reaction mixture was filtered over Harbolite to remove the catalyst and the catalyst was washed with water (60 mL). A sample of the filtrate was taken for analysis. The pH of the remaining filtrate was pH adjusted to 9.0-9.5 (meter) with 0.88 ammonia solution:water (1:1 v/v) (56 mL). The pH was rechecked after 10 min stirring (pH 9.37) and the mixture was cooled in an ice bath (0-5° C.) for 2 h. The solid was filtered and washed with water (30 mL), followed by Alcohol M (30 mL). The solid was pulled dry to give crude oxycodone base. A sample of the crude material was taken for analysis. The remaining solid was charged to a flask and slurried with Alcohol M (353 mL) at reflux for 1 h. The slurry was allowed to cool to room temperature and cooled further to 0-5° C. with an ice bath. The oxycodone base was filtered and washed with cold Alcohol M (98.1 mL), pulled dry and dried at 55° C. overnight. A sample of oxycodone base was taken for analysis and 10 g of the base used to make the hydrochloride salt. A sample of the oxycodone hydrochloride was also analysed.

| 6α-Oxycodol in Post Hydrogenation Liquor (area %)‡ | 6α-Oxycodol in Crude Oxycodone Base (area %)‡ | 6α-Oxycodol in Isolated Oxycodone (area %)‡ | 6α-Oxycodol in Oxycodone HCl (area %)‡ |
|---|---|---|---|
| 0.7 | 0.36 | 0.12 | 0.03 |

| ABUK§ in Post Hydrogenation Liquor (ppm)# | ABUK§ in Crude Oxycodone Base (ppm)# | ABUK§ in Isolated Oxycodone Base (ppm)# | ABUK§ in Oxycodone HCl (ppm)# |
|---|---|---|---|
| <1 | <1 | <1 | 2 |

‡HPLC method = Oxycodone Hydrochloride PhEur 6.0 Method.
§ABUK = 14-hydroxycodeinone, no codeinone was detected.
LCMS (an unvalidated method) was used to analyse the ABUK levels.

The results indicate that even though poorer quality 14-hydroxycodeinone was used as the starting material, the quantities of 6α-oxycodol in the post hydrogenation liquor and crude base are still lower than the quantities of 6α-oxycodol produced in an ambient temperature hydrogenation (for example, compare the 6α-oxycodol levels in Example 1). In addition, the quantities of 6α-oxycodol present in the isolated oxycodone and hydrochloride salt are also well below the NMT 0.25% standard specified in the USP 33 Reissue for Oxycodone Hydrochloride. Furthermore, the ABUK levels at all stages of the reaction are very low.

Example 6 (According to the Invention)

Evaluation of the Effects of Temperature and Hold Time Before Addition of Hydrogen Three hot hydrogenation experiments were performed with experimental conditions and yields as shown in the table (below) using the same batch of 14-hydroxycodeinone and the same ratio of acetic acid and water to evaluate the effects of temperature and hold time before the addition of hydrogen on the levels of 6α-oxycodol and ABUK in the oxycodone base thus produced. The HCl salts were generated from the bases and were evaluated for the levels of ABUK.

| Expt | SM* (g) | Water (g) | Acetic acid (g) | Pd/C (g) | Temp range (° C.) | Hold time before H₂ addition | Isolation change | LOD Yield (g) | Yield (%) |
|---|---|---|---|---|---|---|---|---|---|
| 1 | 4.15 | 13.3 | 1.67 | 0.04 | 80 ± 5 | 15 min | a | 3.60 | 86 |
| 2 | 6 | 19.23 | 2.41 | 0.06 | 80 ± 5 | 6 h | b | 2.36 | 78 |
| 3 | 6 | 19.23 | 2.41 | 0.06 | 60 ± 5 | 6 h | a | 5.44 | 90 |

*SM = starting material = 14-hydrocodeinone
aAs per procedure below
bHalf of reaction mixture taken forward after hydrogenation The general procedure used for the hydrogenation of 14-hydroxycodeinone to form oxycodone base and subsequent salt formation of the oxycodone HCl salt is as outlined below, except where indicated otherwise.

Hot Hydrogenation of 14-Hydroxycodeinone

14-Hydroxycodeinone was charged to a glass pressure vessel followed by water (3.21 g water per gram of 14-hydroxycodeinone) and acetic acid (0.40 g per gram of 14-hydroxycodeinone) forming a solution. Pd/C (10%, dry) (0.01 g Pd/C per gram of 14-hydroxycodeinone) was then added under nitrogen. The resulting mixture was evacuated and the vacuum released with nitrogen three times. The system was then evacuated and heated to the desired temperature (see table). It was held at the desired temperature for 15 min-6 h as shown in the table and hydrogen was then added to 40 psi. The reaction was held for 23 h, purged with nitrogen and sampled. The reaction mixture was cooled to ambient and filtered over a celite bed (0.3 g of celite per gram of 14-hydroxycodeinone). The celite bed was washed with water twice (1.20 g per gram 14-hydroxycodeinone). The combined filtrate was filtered using a 0.22-micron Durapore PVDF membrane filter. The filter was rinsed with water (1.20 g per gram of 14-hydroxycodeinone). The combined filtrate was cooled to <10° C. and adjusted to pH 9-10 with ammonium hydroxide-water (1:1 wt/wt). The mixture was stirred for 1-2 h and filtered. The filter cake was washed with water (1 g 14-hydroxycodeinone/2.41 g water) twice, followed by ethanol (1 g 14-hydroxycodeinone/1.93 g ethanol) twice. The cake was sampled and a LOD performed and the yield determined. Three experiments were performed. The HPLC analysis of the products using HPLC Method 2 are shown below.

Note: in experiment 2, half of the filtrate after the hydrogenation was taken forward and treated as described above.

Oxycodone HCl Salt Formation

Oxycodone base was charged to water (0.63 g per gram of oxycodone base) and ethanol (2.1 g per gram of oxycodone base). The resulting slurry was heated to 60° C. and a 1:1 (v/v) of ethanol-HCl (0.5-0.6 g per gram) of oxycodone base) was added to adjust the pH of the mixture to 2-5, resulting in a solution. The resulting solution was then cooled to ambient (solid precipitated at 40-46° C.) and then to 0-5° C. and filtered. The cake was washed twice with ethanol (1 g oxycodone HCl/1 g EtOH) and then dried at 55° C. under vacuum. The HPLC and ABUK levels are shown below.

| Experiment | Hydrogenation conditions | 6α-Oxycodol in Oxycodone base‡,* (% AUC) | 6α-Oxycodol in Oxycodone HCl* (% AUC) | ABUK§ in Oxycodone base** (ppm) | ABUK§ in Oxycodone HCl** (ppm) |
|---|---|---|---|---|---|
| 1 | 15 min hold at 80° C. prior to introducing H₂ | 0.16 | 0.11 | 1 | 10 |

-continued

| Experiment | Hydrogenation conditions | 6α-Oxycodol in Oxycodone base‡,* (% AUC) | 6α-Oxycodol in Oxycodone HCl* (% AUC) | ABUK§ in Oxycodone base** (ppm) | ABUK§ in Oxycodone HCl** (ppm) |
|---|---|---|---|---|---|
| 2 | 6 h hold at 80° C. prior to introducing H₂ | 0.15 | 0.17 | 1 | 4 |
| 3 | 6 h hold at 60° C. prior | 0.13 | 0.18 | 44 | 20 |

| Experiment | Hydrogenation conditions | 6α-Oxycodol in Oxycodone base‡,* (% AUC) | 6α-Oxycodol in Oxycodone HCl* (% AUC) | ABUK§ in Oxycodone base** (ppm) | ABUK§ in Oxycodone HCl** (ppm) |
|---|---|---|---|---|---|
| | to introducing H₂ | | | | |

‡LOD sample
§ABUK = 14-hydroxycodeinone
*HPLC Method 2
**UPLC/MS-SIM Method

The results from the three hydrogenation reactions show the following:
- There is little change in 6α-oxycodol produced at 80° C. if the reaction mixture is held for 6 hours before hydrogen introduction.
- When a hold period is introduced, the change in hydrogenation temperature from 60 to 80° C. has little effect.
- The % AUC of the 6α-oxycodol impurity in oxycodone base does not change significantly after formation of the HCl salt.

Example 7 (Comparative)

Hydrogenation with Hydrogen Addition at 20±5° C. and Warming to 80±5° C.

A mixture of dry 14-hydroxycodeinone (9.5 g dry) and damp 14-hydroxycodeinone (8.5 g by LOD) was charged to a reactor and triturated with water (150 g) (to enable blending) for 15 min. The resulting slurry was filtered and a sample of the cake dried at 50° C. under vacuum (0.39 g) for analysis. The remaining wet cake (assumed 17.5 g) was charged to a stainless steel Parr pressure vessel followed by water (48.37 g to give a total water of 54.84 g accounting for the water in the starting material) and acetic acid (7.21 g, 2.15 equivalents) forming a solution. Pd/C (10%, dry, 0.16 g, ~0.01 g Pd/C per gram of 14-hydroxycodeinone) was then added under nitrogen, rinsing the sides of the flask with water (1.16 g, 0.07 g/g of 14-hydroxycodeinone). The resulting mixture was evacuated and the vacuum released with nitrogen three times. It was again evacuated and hydrogen was added with the mixture at 17° C. (target 20±5° C.) up to 40 psi (target 40±2 psi). There was a one degree change in temperature after 2 minutes. The temperature gradually crept up to 28° C. over 50 minutes. Heating was applied to the mixture after reaching 28° C., getting to 80±5° C., over 2 h. The reaction was held at 80±5° C./40 psi for approximately 18 h (total time of 21 h after hydrogen addition) and sampled (see table) showing 4.60 area % of 6α-oxycodol. Thus, it can be seen that the addition of hydrogen at low temperature gives relatively higher levels of 6α-oxycodol compared to adding hydrogen at a higher temperature.

The batch was cooled to 9° C. (target 10±2° C.) and adjusted to pH 9.48 with 1:1 (wt/wt) ammonium hydroxide-water and stirred for 1 h at 12.6° C. The mixture was filtered (Buchner funnel/vacuum) and the cake washed with water (2×17.5 g). A sample of the cake was dried (0.73 g) and HPLC analysis gave 6α-oxycodol at 2.40 area %, indicating that, while there was almost a 50% loss in area % of the 6α-oxycodol during isolation, the level of 6α-oxycodol remained relatively high.

| Peak ID | RRT | Reaction completion (% AUC)* | Isolated base (% AUC)* |
|---|---|---|---|
| | 0.42 | 0.15 | 0.06 |
| | 0.44 | 0.15 | ND¹ |
| | 0.51 | 0.21 | ND |
| 6α-Oxycodol | 0.59 | 4.61 | 2.40 |
| | 0.61 | 0.41 | ND |
| | 0.67 | 0.89 | 0.56 |
| | 0.80 | 3.75 | 0.92 |
| Oxycodone | 1.00 | 89.62 | 95.87 |
| | 1.97 | 0.23 | 0.19 |

¹ND = not detected
*HPLC Method 2

The results show that a significant amount of 6α-oxycodol (4.61%) was formed by adding hydrogen at low temperature (20±5° C.) and, as such, further processing of the product would be required in order to reduce this level down to a specification limit. Each further processing stage would result in yield loss, time and reagents.

Example 8 (According to the Invention)

Acetic Acid with Minimal Amount of Water in the Hydrogenation of 14-Hydroxycodeinone The use of acetic acid with the minimal amount of water (equivalent to the quantity of water present in 10% wet Pd/C catalyst) in the hydrogenation of 14-hydroxycodeinone was explored. It was found that approximately 3 g of acetic acid/g of 14-hydroxycodeinone was needed to effect its dissolution at ambient. 14-Hydroxycodeinone (4.5 g), was dissolved in acetic acid (3 g of acetic acid/g of 14-hydroxycodeinone) and water (approximately the same weight as the amount of dry Pd/C used) were charged to a glass pressure reactor followed by 10% Pd/C catalyst (dry, 0.01 g/g 14-hydroxycodeinone). The hydrogenation was performed as in the above experiments with hydrogen being introduced at 80° C. The reaction was sampled after 23 h showing a very low level (0.14% AUC) of 6α-oxycodol. The isolated oxycodone alkaloid product showed a reduction in the amount of the 6α-oxycodol impurity (0.14 to 0.09% AUC), as well as the other impurities, giving very high purity (99.7% AUC) product. Based on LOD, a yield of 91% was obtained. The ABUK (14-hydroxycodeinone) content of the LOD sample was ≤5 ppm. Recrystallization of the product from DCM/EtOH, yielded Oxycodone base with undetectable level of 6α-oxycodol. Analysis performed using HPLC Method 2 and the UPLC/MS-SIM Method.

Example 9 (According to the Invention)

Ethanol/Water Solvent Mixture

14-Hydroxycodeinone (4.5 g) was warmed with ethanol (2.17 g/g 14-hydroxycodeinone) to 60-65° C. and acetic acid was added in portions until all solid dissolved. Following the addition of 10% Pd/C (dry, 0.01 g/g 14-hydroxycodeinone) and water (0.01 g/g 14-hydroxycodeinone) to compensate for the water in the dry Pd/C catalyst, the hydrogenation was performed with hydrogen being introduced at 80° C. The reaction was sampled after 22 h and was determined to be complete. This reaction resulted in low levels of 6α-oxycodol. After isolation (84% yield by LOD), the level of 6α-oxycodol was also determined to be low by analysis.

| Starting 14-Hydroxycodeinone | Hydrogenation Parameters | | | | | 6α-Oxycodol‡ |
|---|---|---|---|---|---|---|
| | Solvent | Acid | Temp (±5° C.) | Time (h) | Product | |
| 4.5 g | EtOH (2.00)* | HOAc (1.29)* | 80 | 22 | 22 h reaction mixture | 0.37 |
| | H₂O (0.01)* | | | | Oxycodone alkaloid (LOD sample) | 0.18 |

*per gram 14-hydroxycodeinone
‡HPLC Method 2

The invention claimed is:

1. A process for preparing an oxycodone acid adduct, said process comprising hydrogenating an aqueous solution of 14-hydroxycodeinone and an acid to form a solution of the oxycodone acid adduct, wherein the hydrogenation is carried out at one or more temperatures greater than ambient temperature in the presence of a hydrogenation catalyst and hydrogen gas, wherein the solution of oxycodone acid adduct comprises 6α-oxycodol in an amount ≤about 0.800 area % as determined by HPLC.

2. A process according to claim 1, wherein the acid is selected from the group consisting of acetic acid, phosphoric acid, citric acid, tartaric acid, oxalic acid, hydrochloric acid, hydrobromic acid and a mixture thereof.

3. A process according to claim 1 or claim 2, wherein the hydrogenation is carried out at one or more temperatures in the range of ≥about 55° C. to about ≤100° C.

4. A process according to claim 1, wherein the hydrogenation is carried out at one or more temperatures in the range of ≥about 75° C. to about ≤100° C.

5. A process according to claim 4, wherein the hydrogenation is carried out at one or more temperatures in the range of ≥about 77° C. to about ≤85° C.

6. A process according to claim 1, wherein the hydrogenation catalyst is a heterogeneous or homogenous catalyst, preferably a heterogeneous catalyst.

7. A process according to claim 1, wherein the heterogeneous catalyst is a heterogeneous platinum group metal (PGM) catalyst, preferably a heterogeneous palladium catalyst.

8. A process according to claim 1, wherein the solution of oxycodone acid adduct comprises 6α-oxycodol in an amount ≤about 0.250 area % as determined by HPLC.

9. A process according to claim 1, wherein the process further comprises treating the solution of oxycodone acid adduct to form solid oxycodone acid adduct.

10. A process according to claim 9, wherein the process further comprises treating the solid oxycodone acid adduct to form oxycodone alkaloid.

11. A process according to claim 1, wherein the process further comprises treating the solution of oxycodone acid adduct with a base to form oxycodone alkaloid.

12. A process according to claim 10, wherein the oxycodone alkaloid comprises 6α-oxycodol in an amount ≤about 0.250 area % as determined by HPLC.

13. A process according to claim 10, wherein the oxycodone alkaloid comprises ≤about 25 ppm of an α,β-unsaturated ketone.

14. A process according to claim 1, wherein the oxycodone acid adduct comprises ≤about 25 ppm of an α,β-unsaturated ketone.

15. A process according to claim 13, wherein the α,β-unsaturated ketone is selected from the group consisting of 14-hydroxycodeinone, codeinone and a mixture thereof.

16. A process for preparing an oxycodone acid adduct, said process comprising hydrogenating an aqueous solution of 14-hydroxycodeinone and an acid to form a solution of the oxycodone acid adduct, wherein the hydrogenation is carried out at one or more temperatures greater than ambient temperature in the presence of a hydrogenation catalyst and hydrogen gas, wherein the solution of the oxycodone acid adduct comprises less 6α-oxycodol than that produced on carrying out the hydrogenation at ambient temperature.

17. A process for preparing an oxycodone acid adduct, said process comprising hydrogenating 14-hydroxycodeinone and an acid in a solvent comprising an alcohol and optionally water to form the oxycodone acid adduct, wherein the hydrogenation is carried out at one or more temperatures greater than ambient temperature in the presence of a hydrogenation catalyst and hydrogen gas, wherein the oxycodone acid adduct comprises less 6α-oxycodol than that produced on carrying out the hydrogenation at ambient temperature.

18. An aqueous solution of oxycodone acid adduct comprising 6α-oxycodol in an amount ≤about 0.800 area % as determined by HPLC.

19. An aqueous solution according to claim 18, further comprising ≤about 25 ppm of an α,β-unsaturated ketone, preferably ≤about 10 ppm.

20. Solid oxycodone acid adduct comprising 6α-oxycodol in an amount ≤about 0.800 area % as determined by HPLC, preferably ≤about 0.250 area %.

21. A solid oxycodone acid adduct according to claim 20, further comprising ≤about 25 ppm of an α,β-unsaturated ketone, preferably ≤about 10 ppm.

22. Solid oxycodone alkaloid comprising 6α-oxycodol in an amount ≤about 0.800 area % as determined by HPLC, preferably ≤about 0.250 area %.

23. Solid oxycodone alkaloid according to claim 22, further comprising ≤about 25 ppm of an α,β-unsaturated ketone, preferably ≤about 10 ppm.

24. A process according to claim 11, wherein the oxycodone alkaloid comprises 6α-oxycodol in an amount ≤about 0.250 area % as determined by HPLC.

25. A process according to claim 11, wherein the oxycodone alkaloid comprises ≤about 25 ppm of an α,β-unsaturated ketone.

26. A process according to claim 14, wherein the α,β-unsaturated ketone is selected from the group consisting of 14-hydroxycodeinone, codeinone and a mixture thereof.

* * * * *